United States Patent
Bérard et al.

(10) Patent No.: US 9,649,026 B2
(45) Date of Patent: May 16, 2017

(54) COUPLED RECONSTRUCTION OF REFRACTIVE AND OPAQUE SURFACES

(71) Applicant: LUCASFILM ENTERTAINMENT COMPANY LTD., San Francisco, CA (US)

(72) Inventors: Pascal Bérard, Zurich (CH); Thabo Beeler, Zurich (CH); Derek Bradley, Zurich (CH)

(73) Assignees: Disney Enterprises, Inc., Burbank, CA (US); ETH Zürich (Eidgenössische Technische Hochschule Zürich), Zürich (CH)

( * ) Notice: Subject to any disclaimer, the term of this patent is extended or adjusted under 35 U.S.C. 154(b) by 256 days.

(21) Appl. No.: 14/550,751

(22) Filed: Nov. 21, 2014

(65) Prior Publication Data

US 2016/0143524 A1    May 26, 2016

(51) Int. Cl.
   *G06K 9/00*    (2006.01)
   *A61B 3/103*   (2006.01)
   *A61B 3/117*   (2006.01)

(52) U.S. Cl.
   CPC .............. *A61B 3/103* (2013.01); *A61B 3/117* (2013.01)

(58) Field of Classification Search
   CPC ....... A61B 3/103; A61B 3/1005; A61B 3/107; A61B 3/112; A61B 3/117; A61B 3/12; A61B 6/032; G06K 9/00617; G06K 9/4661; G06K 9/0061; G06T 2207/30041; G06T 7/0046
   See application file for complete search history.

(56) References Cited

U.S. PATENT DOCUMENTS

| | | | | |
|---|---|---|---|---|
| 5,929,968 A | * | 7/1999 | Cotie | G02C 7/04 351/159.02 |
| 8,824,779 B1 | * | 9/2014 | Smyth | G06K 9/0061 382/100 |
| 2007/0222948 A1 | * | 9/2007 | Dai | A61B 3/1015 351/212 |

(Continued)

OTHER PUBLICATIONS

Guillaume Francois, ("Image-Based Modeling of the Human Eye", IEEE Transactions on Visualization and Computer Graphics, vol. 5, Sep./Oct. 2009).*

(Continued)

*Primary Examiner* — Amara Abdi
(74) *Attorney, Agent, or Firm* — Kilpatrick Townsend & Stockton LLP

(57) ABSTRACT

Systems and techniques for reconstructing one or more surfaces of an object including one or more opaque surfaces behind one or more refractive surfaces are provided. The systems and techniques may include obtaining one or more images of the object including an opaque surface located behind a refractive surface and determining one or more refractive surface constraints using the one or more images. The one or more refractive surface constraints constrain one or more characteristics of the refractive surface. The systems and techniques may further include reconstructing an opaque surface representation or a refractive surface representation using the one or more refractive surface constraints, the opaque surface representation representing the opaque surface of the object, and the refractive surface representation representing the refractive surface of the object.

20 Claims, 32 Drawing Sheets

(56) References Cited

U.S. PATENT DOCUMENTS

| | | | |
|---|---|---|---|
| 2009/0135372 A1* | 5/2009 | Sarver | A61B 3/1015 351/212 |
| 2010/0004537 A1* | 1/2010 | Eilers | A61B 8/0858 600/443 |
| 2011/0032533 A1* | 2/2011 | Izatt | G01B 11/2441 356/497 |
| 2013/0010260 A1* | 1/2013 | Tumlinson | A61B 3/152 351/206 |
| 2014/0009741 A1* | 1/2014 | Levien | A61B 3/102 351/206 |
| 2014/0355841 A1* | 12/2014 | Santos-Villalobos | G06K 9/0061 382/117 |

OTHER PUBLICATIONS

Alexander, O. et al., "The digital Emily project: Achieving a photorealistic digital actor," IEEE CG&A 30, 4, 20-31, (2010).

Ares, M. et al., "Comparison of cubic b-spline and zernike-fitting techniques in complex wavefront reconstruction," Applied optics 45, 27, 6954-6964, (2006).

Atcheson, B. et al., "CALTag: High precision fiducial markers for camera calibration," In International Workshop on Vision, Modeling and Visualization, (2010).

Atchison, D. A. et al., "Eye shape in emmetropia andmyopia," Investigative Ophthalmology & Visual Science 45, 10, 3380-3386, (2004).

Beeler, T. et al., "High-Quality Single-Shot Capture of Facial Geometry," ACM Trans, Graphics (Proc. SIGGRAPH) 29, 40:1-40:9, (2010).

Beeler, T. et al., "High-quality passive facial performance capture using anchor frames," ACM Trans. Graphics (Proc. SIGGRAPH) 30, 4, 75, (2011).

Beeler, T. et al., "Coupled 3D reconstruction of sparse facial hair and skin," ACM Trans. Graphics (Proc. SIGGRAPH) 31, 4, 117:1-117:10, (2012).

Besl, P. J. et al., "A method for registration of 3-d shapes," IEEE Trans. on PAMI 14, 2, 239-256, (1992).

Blanz, V. et al., A morphable model for the synthesis of 3d faces. In Proceedings of the 26th annual conference on Computer graphics and interactive techniques, 187-194, (1999).

Bradley, D. et al., High resolution passive facial performance capture. ACM Trans. Graphics (Proc. SIGGRAPH) 29, 4, 41, (2010).

Brox, T. et al., "High Accuracy Optical Flow Estimation Based on a Theory for Warping," ECCV, Springer, 25-36, (2004).

Eagle Jr, R., "Iris pigmentation and pigmented lesions: an ultrastructural study," Trans. of the American Ophthalmological Society 86, 581, (1988).

Efros, A. et al., "Texture Synthesis by Non-Parametric Sampling," IEEE ICCV, 1033-1038, (1999).

François, G. et al., "Image-based modeling of the human eye," IEEE TVCG 15, 5, 815-827, (2009).

Garrido, P. et al., "Reconstructing detailed dynamic face geometry from monocular video," ACM Trans. Graphics (Proc. SIGGRAPH Asia) 32, 6, 158, (2013).

Ghosh, A. et al., "Multiview face capture using polarized spherical gradient illumination," ACM Trans. Graphics (Proc. SIGGRAPH Asia) 30, 6, 129, (2011).

Halstead, M. A. et al., "Reconstructing curved surfaces from specular reflection patterns using spline surface fitting of normals," In Proceedings of Computer graphics and interactive techniques, 335-342, (1996).

Haralick, R. M., "Statistical and structural approaches to texture," Proc. IEEE 67, 5, 786-804, (1979).

Hernández, C. et al., "Multiview photometric stereo," IEEE PAMI 30, 3, 548-554, (2008).

Ma, W.-C. et al., "Rapid acquisition of specular and diffuse normal maps from polarized spherical gradient illumination," In Proc. Rendering Techniques, 183-194, (2007).

Sorkine et al., "Laplacian Surface Editing," In Proc. SGP, 175-184, (2004).

\* cited by examiner

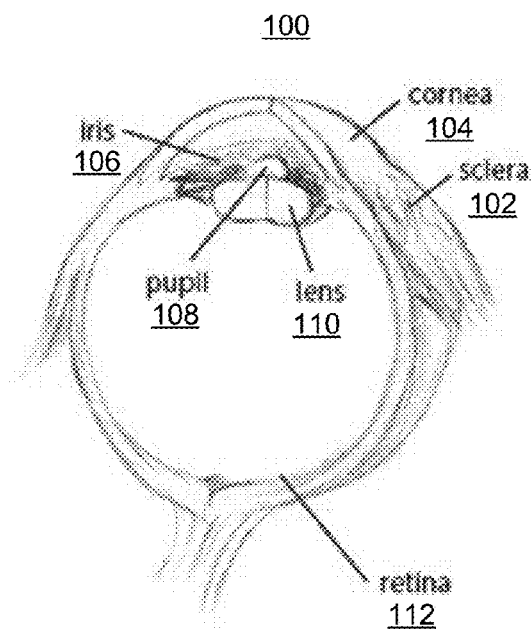
FIG. 1
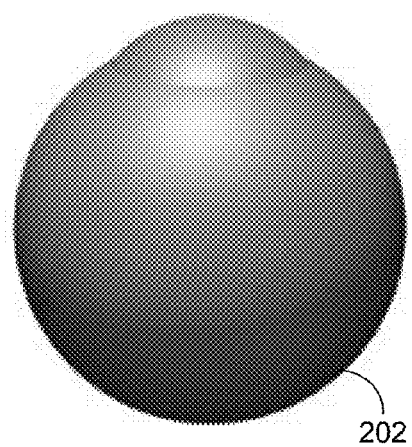 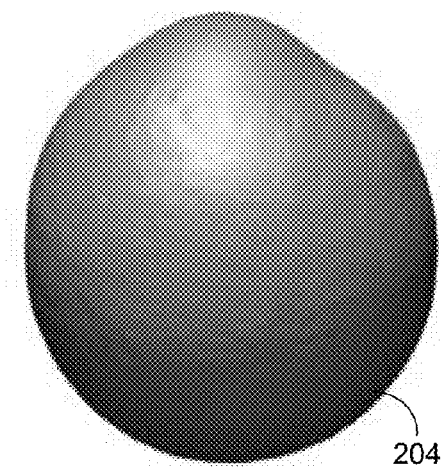
FIG. 2A  FIG. 2B

400

COUPLED RECONSTRUCTION OF REFRACTIVE AND OPAQUE SURFACES

FIELD

The present disclosure generally relates to reconstructing one or more refractive and/or opaque surfaces. For example, one or more opaque surfaces of an object or one or more refractive surfaces that may be part of the object may be reconstructed for use in rendering an animation of the object.

BACKGROUND

Many objects include one or more refractive surfaces that refract light that is incident on the surface. For example, glass, water, a cornea part of an eye, as well as many other objects, include refractive surfaces. The refractive nature of the refractive surface causes the refractive surface, and any surface behind the refractive surface, to appear visually distorted.

One example of an object that includes a refractive surface includes an eye. Techniques for producing digital doubles in computer graphics tend to give little attention to details of a subject's eye. These techniques typically focus on reconstructing a skin surface of a subject and the appearance of the skin in increasing levels of detail. The visible portion of the eye is comprised of the white sclera, the transparent cornea, and the colored iris. Generic eye models used in computer graphics are insufficient for capturing the individual identity of a digital human. A manual process may be needed to create digital representations of eyes of characters, which requires a significant amount of effort.

SUMMARY

Techniques and systems are described for obtaining a high quality capture of an object. In some examples, a reconstruction system and technique is provided for reconstructing an unknown surface of the object that is located behind a refractive surface. The refractive nature of the refractive surface causes the refractive surface, and any surface behind the refractive surface, to appear visually distorted. One or more surface constraints of the refractive surface may be determined based on one or more captured images. The one or more surface constraints may be used to reconstruct the unknown surface and may also be used to reconstruct the refractive surface.

In one example, the transparent cornea of an eye is a refractive surface, and the iris is an opaque surface that is located behind the refractive cornea. In some examples, capture techniques and systems are provided that accurately reconstruct one or more visible parts of an eye, including the sclera, the transparent cornea, and the non-rigidly deforming colored iris. A hybrid reconstruction technique addresses these different parts individually, and a complete model of an eye is generated that includes both spatio-temporal shape and texture at detailed levels, enabling the creation of more realistic digital representations of subjects. The reconstruction techniques and systems described herein can greatly reduce the time spent reconstructing a representation of a subject's eye while increasing the realistic appearance of the eye representation.

In some examples, a reconstruction technique for reconstructing a representation of a subject's eye may capture an overall shape and spatial surface variation of a sclera of the subject's eye, including a detailed vein texture. The reconstruction technique may further capture the complex shape, texture, and deformation of the iris. Even further, the reconstruction technique may capture properties of the transparent cornea, including the curvature of the cornea and the refractive index of the medium inside the eye. The reconstruction technique addresses the sclera, cornea, and iris individually while respecting interdependencies of the different parts. For example, the technique may recover the sclera shape, followed by the cornea, and finally the iris. Each stage of the reconstruction requires a different approach, relying on constraints from the previous stages, but tuned to the appearance properties in the current stage. The various reconstruction techniques also require different (but complementary) capture data, which may be acquired through a hardware setup of cameras, flashes, and lights (e.g., light-emitting diodes).

According to at least one example, a computer-implemented method of reconstructing one or more surfaces of an object including one or more opaque surfaces behind one or more refractive surfaces may be provided that includes obtaining one or more images of the object, the object including an opaque surface located behind a refractive surface. The method further includes determining one or more refractive surface constraints using the one or more images, the one or more refractive surface constraints constraining one or more characteristics of the refractive surface. The method further includes reconstructing an opaque surface representation or a refractive surface representation using the one or more refractive surface constraints, the opaque surface representation representing the opaque surface of the object, and the refractive surface representation representing the refractive surface of the object.

In some embodiments, a system may be provided for reconstructing one or more surfaces of an object including one or more opaque surfaces behind one or more refractive surfaces. The system includes a memory storing a plurality of instructions and one or more processors. The one or more processors are configurable to: obtain one or more images of the object, the object including an opaque surface located behind a refractive surface; determine one or more refractive surface constraints using the one or more images, the one or more refractive surface constraints constraining one or more characteristics of the refractive surface; and reconstruct an opaque surface representation or a refractive surface representation using the one or more refractive surface constraints, the opaque surface representation representing the opaque surface of the object, and the refractive surface representation representing the refractive surface of the object.

In some embodiments, a computer-readable memory storing a plurality of instructions executable by one or more processors may be provided. The plurality of instructions comprise: instructions that cause the one or more processors to obtain one or more images of the object, the object including an opaque surface located behind a refractive surface; instructions that cause the one or more processors to determine one or more refractive surface constraints using the one or more images, the one or more refractive surface constraints constraining one or more characteristics of the refractive surface; and instructions that cause the one or more processors to reconstruct an opaque surface representation or a refractive surface representation using the one or more refractive surface constraints, the opaque surface representation representing the opaque surface of the object, and the refractive surface representation representing the refractive surface of the object.

In some embodiments, the method, system, and computer-readable memory described above for reconstructing one or more surfaces of an object including one or more opaque surfaces behind one or more refractive surfaces may further include wherein reconstructing the opaque surface representation includes undoing distortion introduced by the refractive surface. In some embodiments, reconstructing the refractive surface representation includes employing an optimization method using the one or more surface constraints.

In some embodiments, the one or more refractive surface constraints include one or more reflection constraints, one or more refraction constraints, or one or more position constraints. In some embodiments, the one or more characteristics of the refractive surface include a position or a surface normal of the refractive surface. In some embodiments, the one or more reflection constraints are obtained by shining one or more lights onto the refractive surface.

In some embodiments, the object includes an eye, the refractive surface includes a cornea part of the eye, and the opaque surface includes an iris part of the eye. In some embodiments, the method, system, and computer-readable memory described above includes reconstructing a sclera representation using the one or more images, the sclera representation representing a sclera part of the eye.

In some embodiments, the object is submerged under water and the refractive surface includes a surface of the water. In some embodiments, the object is cast under a layer of material and the refractive surface includes a surface of the material.

According to at least one example, a computer-implemented method of reconstructing parts of an eye of a subject may be provided that includes obtaining one or more images of the eye of the subject, and determining one or more cornea surface constraints. The method further includes reconstructing a cornea representation or an iris representation using the one or more cornea surface constraints, the cornea representation representing a cornea part of the eye, and the iris representation representing an iris part of the eye.

In some embodiments, a system for reconstructing parts of an eye of a subject may be provided that includes a memory storing a plurality of instructions and one or more processors. The one or more processors are configurable to: obtain one or more images of the eye of the subject; determine one or more cornea surface constraints; and reconstruct a cornea representation or an iris representation using the one or more cornea surface constraints, the cornea representation representing a cornea part of the eye, and the iris representation representing an iris part of the eye.

In some embodiments, a computer-readable memory storing a plurality of instructions executable by one or more processors may be provided. The plurality of instructions comprise: instructions that cause the one or more processors to obtain one or more images of the eye of the subject; instructions that cause the one or more processors to determine one or more cornea surface constraints; and instructions that cause the one or more processors to reconstruct a cornea representation or an iris representation using the one or more cornea surface constraints, the cornea representation representing a cornea part of the eye, and the iris representation representing an iris part of the eye.

In some embodiments, the method, system, and computer-readable memory described above for reconstructing parts of an eye of a subject may further include reconstructing a sclera representation using the one or more images of the eye, the sclera representation representing a sclera part of the eye. In some embodiments, reconstructing the sclera representation using the one or more images of the eye includes: segmenting the one or more images of the eye to identify the sclera part, the cornea part, and the iris part of the eye in the one or more images; generating one or more mesh representations of the sclera part, wherein a mesh representation of the sclera part is generated by projecting a segmented image of the eye onto a mesh representation of the eye; aligning poses in the one or more mesh representations of the sclera part to a reference pose; and merging the one or more mesh representations of the sclera into a merged sclera mesh.

In some embodiments, reconstructing the cornea representation includes employing an optimization method using the one or more cornea surface constraints.

In some embodiments, reconstructing the iris representation includes: detecting a boundary of a pupil part of the eye using a segmented image of the eye; refining the boundary of the pupil by generating a ray from a point on the boundary of the pupil part, refracting the ray using a refraction index, and intersecting corresponding rays from the point in multiple images of the pupil from multiple camera views; and determining a topology of a mesh representation of the iris part using the refined boundary of the pupil.

In some embodiments, the one or more cornea surface constraints include one or more reflection constraints, one or more refraction constraints, or one or more position constraints. In some embodiments, the one or more reflection constraints are obtained by shining one or more lights onto the cornea part of the eye. In some embodiments, the one or more position constraints are obtained from a merged sclera mesh.

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will be described in more detail below in the following specification, claims, and accompanying drawings.

BRIEF DESCRIPTION OF DRAWINGS

Illustrative embodiments of the present invention are described in detail below with reference to the following drawing figures:

FIG. 1 illustrates a schematic of a human eye, in accordance with an embodiment of the present invention.

FIG. 2A illustrates an example of an eye representation generated using a low order approximation technique.

FIG. 2B illustrates an example of an eye representation generated using the reconstruction techniques described herein, in accordance with an embodiment of the present invention.

DETAILED DESCRIPTION

Figure 3:
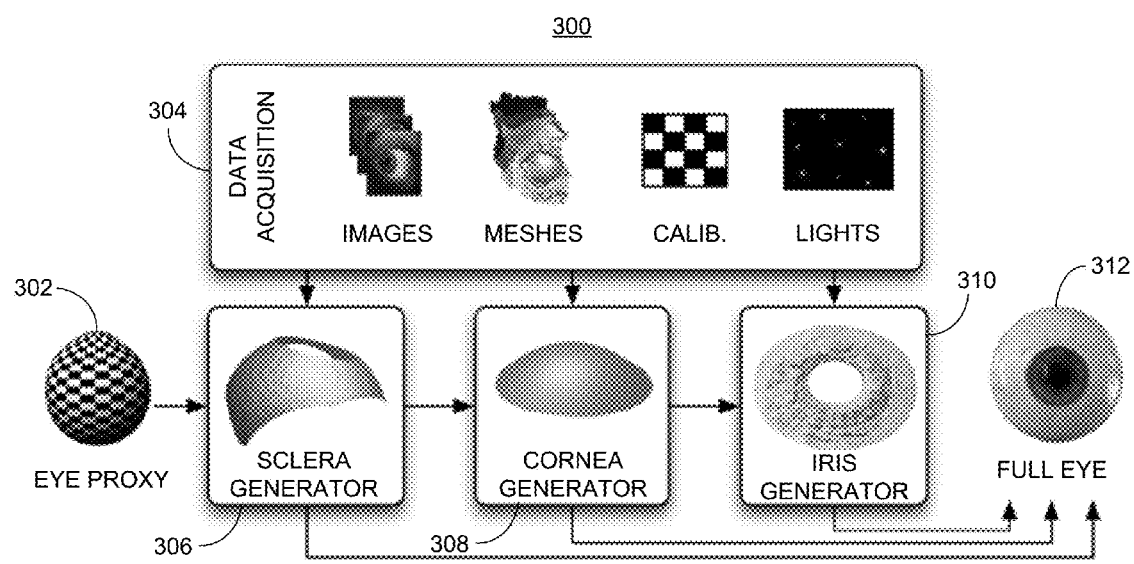
FIG. 3 illustrates an example of a system for reconstructing parts of an eye of a subject, in accordance with an embodiment of the present invention.

In the following description, for the purposes of explanation, specific details are set forth in order to provide a thorough understanding of embodiments of the invention. However, it will be apparent that various embodiments may be practiced without these specific details. The figures and description are not intended to be restrictive.

The ensuing description provides exemplary embodiments only, and is not intended to limit the scope, applicability, or configuration of the disclosure. Rather, the ensuing description of the exemplary embodiments will provide those skilled in the art with an enabling description for implementing an exemplary embodiment. It should be understood that various changes may be made in the function and arrangement of elements without departing from the spirit and scope of the invention as set forth in the appended claims.

Many objects have a refractive surface that refracts light incident on the refractive surface. For example, glass, water, a cornea part of an eye, as well as many other objects, include refractive surfaces. The refractive nature of the refractive surface causes the refractive surface, and any surface behind the refractive surface, to appear visually distorted. Techniques and systems are described for obtaining a high quality capture of an object that includes an unknown opaque surface, and that includes or is located behind a refractive surface. As described in more detail below, images of the object may be used to obtain one or more refractive surface constraints that constrain one or more characteristics of the refractive surface. The one or more refractive surface constraints can then be used to reconstruct a surface of the object that is located behind the refractive surface and/or to reconstruct the refractive surface.

One example of an object that includes a refractive surface and an opaque surface located behind the refractive surface is an eye. Due to these features, a digital representation of an eye is difficult to accurately generate. Creating photo-realistic digital humans is a long-standing challenge in computer graphics. One of the cornerstones of producing digital doubles is capturing a subject's face. Techniques for producing digital doubles in computer graphics typically focus on reconstructing the skin surface of a subject and its appearance in increasing levels of detail. However, the eye receives very little attention in computer graphics, such as the shape of the eye. Every eye has unique individuality. FIG. 1 illustrates an example of an eye 100 that includes a sclera 102, a cornea 104, an iris 106, a pupil 108, a lens 110, and a retina 112. The visible portion of the eye 100 is comprised of the sclera 102, the cornea 104, and the iris 106. Each of these visible portions includes unique features for different individuals. However, the individuality of the eye is not considered in common techniques for three-dimensional (3D) eye generation. While the eye is a central feature of individual appearance, its shape is typically approximated in computer graphics with gross simplifications. FIG. 2A illustrates an example of a digital representation 202 of an eye generated using a low order approximation technique. For example, the shape of the eye 202 may be generally approximated in computer graphics using one or more spheres, such as a larger sphere for the sclera and a smaller sphere for the cornea. Further, the iris is often thought of as a planar disc, or as a cone to simulate the refraction of the cornea. The constriction and dilation of the pupil is typically modeled as planar, radial motion, and the out-of-plane deformation of the iris is generally neglected. Such generic eye models used in computer graphics are insufficient for capturing the individual identity of a digital human. While a simple modeled or simulated eye may be sufficient for background characters, current industry practices spend significant effort to manually create eyes of hero characters.

The example illustrated in FIG. 2A demonstrates that the aforementioned assumptions only roughly approximate the true physiology of an eye, and thus cannot represent subject-specific details that can greatly increase the realism of a digital double of the subject. Furthermore, the eyeball exhibits strong asymmetry, and contains microscopic surface details and imperfections that are subject-specific. For example, a Pingueculas includes a degeneration of the fibers of the sclera that results in a small bump on a subject's eye. As another example, the micro-geometry of the iris is as unique to every person as a fingerprint, and its position and deformation depends on the accommodation of the underlying lens. These are just a few examples of eye details that cannot be captured with traditional models. Other examples will be described herein, for example details that occur based on the dynamic deformation of the iris during pupillary response when varying pupil sizes occur due to relaxation and contraction of the iris dilator muscle.

To overcome the limitations of generic eye models and to accurately reproduce the intricacies of a human eye, reconstruction techniques described herein can be used to capture and reconstruct eyes from images of real human subjects. These same reconstruction techniques can be used to reconstruct other objects that also include an unknown surface that are located behind a refractive surface.

The eye is more complex than skin, which is often assumed to be a diffuse Lambertian surface in reconstruction methods. The human eye is a heterogeneous compound of opaque and transparent surfaces with a continuous transition between the two, and has surfaces that are visually distorted due to refraction. The complex nature of an eye makes capturing the eye very challenging, requiring a novel technique that combines several complementary techniques for image-based reconstruction. Reconstruction techniques described herein focus on the appearance properties of the different components of the eye, and include different strategies for reconstructing each component. For example, while it may be possible to assume that the sclera is diffuse and Lambertian, the cornea is completely transparent, and the iris is viewed under unknown distortion due to refraction. Furthermore, there is a coupling of the eye components, for example the corneal shape should transition smoothly to the sclera, and the perceived iris position depends on both the corneal shape as well as the exact index of refraction (both of which vary from person to person).

Accordingly, the reconstruction techniques described herein are used to accurately reconstruct all the visible parts of the eye, including the white sclera, the transparent cornea, and the non-rigidly deforming colored iris. The sclera, cornea, and iris exhibit very different appearance properties. The reconstruction techniques address these different parts individually to reconstruct a representation of a subject's eye or eyeball. As used herein, the terms eye and eyeball may be used interchangeably. A complete model is generated that includes both spatio-temporal shape and texture at great levels of detail, enabling the creation of more believable digital representations of subjects. These reconstruction techniques not only allows the creation of more realistic digital doubles for visual effects and digital media by scanning real subjects (e.g., an actor or other subject), but it also provides the ability to capture the accurate spatiotemporal shape of an eye in-vivo. FIG. 2B illustrates an example of a representation 204 of an eye generated using the reconstruction techniques described herein.

The reconstruction techniques allow reconstruction of the unique intricacies of the subject's eye. For example, a reconstruction technique may capture an overall shape and spatial surface variation of a sclera of the subject's eye, including a detailed vein texture. The reconstruction technique may further capture the complex shape, texture, and deformation of the iris. The reconstruction technique may also capture properties of the transparent cornea, including the curvature of the cornea and the refractive index of the medium inside the eye. Using such a technique, the sclera, cornea, and iris are addressed individually while interdependencies of the different parts are respected. For example, the technique may recover the sclera shape, followed by the cornea, and finally the iris. Each stage of the reconstruction requires a different approach, relying on constraints from the previous stages, but tuned to the appearance properties in the current stage. The various reconstruction techniques also require different (but complementary) capture data, which may be acquired through a hardware setup of cameras, flashes, and lights (e.g., light-emitting diodes).

In some examples, the reconstruction technique may reconstruct the entire visible part of the sclera by capturing the eyeball in different poses in which the eyelids occlude a different part of the sclera. These mainly diffuse sclera parts may be reconstructed, at least in part, using a multi-stereo view system, and may be combined together with a proxy eyeball to reconstruct a full-textured eyeball. Occluded or missing texture regions may be synthesized. In some examples, the transparent cornea may be reconstructed using a hybrid shape-from-specularity technique and a shape-from-distortion technique. A set of position, reflection, and refraction constraints may be defined that constrain either the position or the surface normal of the cornea. These constraints are only jointly satisfied at the true position of the cornea. In some embodiments, the reflection constraints may be obtained from a sparse set of colored lights, such as a set of light emitting diodes (LEDs) or other suitable light source. In some embodiments, the refraction constraints may be computed by extracting corresponding iris points from one or more input images. Using a sparse set of lights instead of a dense illumination pattern allows the underlying iris to contribute to the optimization in the form of the refraction constraints, allowing an estimation of the index of refraction and reconstruction of the shape of the iris from the same data. In some examples, the iris geometry may be reconstructed by tracing corresponding image points through the refracting cornea. To capture the deformation of the iris during dilation and contraction, a series of images with increasing pupil size may be acquired, which is then brought into vertex-correspondence using optical flow techniques. The reconstruction techniques described herein greatly reduce the time spent to generate digital representations of eyes, and help to increase the realism of the eyes. Further details of the reconstruction techniques will be described herein.

FIG. 3 illustrates an example of a system 300 for reconstructing one or more surfaces of an object, such as one or more parts of an eye of a subject. Several modalities of data are acquired using a data acquisition system 304. Data may include images, meshes, calibration information, lighting input, and any other appropriate data. Some or all of the data acquired using data acquisition system 304 and/or an eye proxy 302 are used as input to a sclera generator 306, a cornea generator 308, and an iris generator 310 to reconstruct representations of a sclera part, a cornea part, and an iris part of the subject's eye. The representations of the sclera part, cornea part, and iris part are combined into a complete eye model 312.

The eye reconstruction techniques first obtain high-quality imagery of a subject's eye that is to be reconstructed to generate a representation of the eye. Human eyes are small, mostly occluded by the face, and have complex appearance properties. Additionally, it may be difficult for a subject to keep their eye position fixed for extended periods of time. These factors make capturing high-quality imagery of the eye challenging. Accordingly, a unique acquisition setup is provided that can image the eye with variation in gaze, focus, and pupil dilation. One of ordinary skill in the art will appreciate that images of both eyes of the subject may be captured using the data acquisition setup.

Figure 4A:
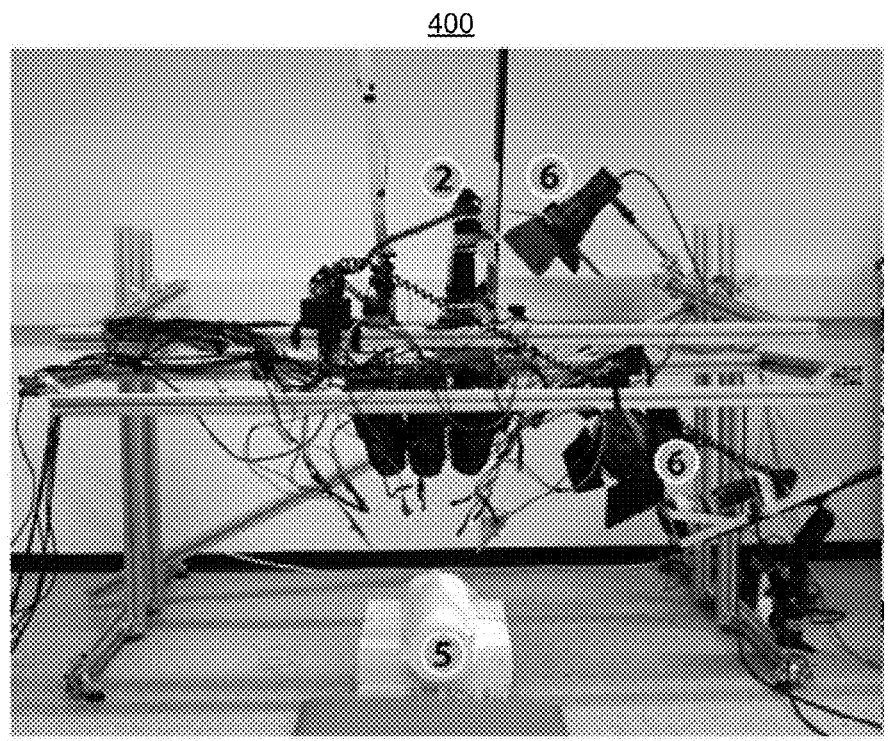
FIG. 4A illustrates an example of a system for acquiring data used in an eye reconstruction technique, in accordance with an embodiment of the present invention.
Figure 4B:
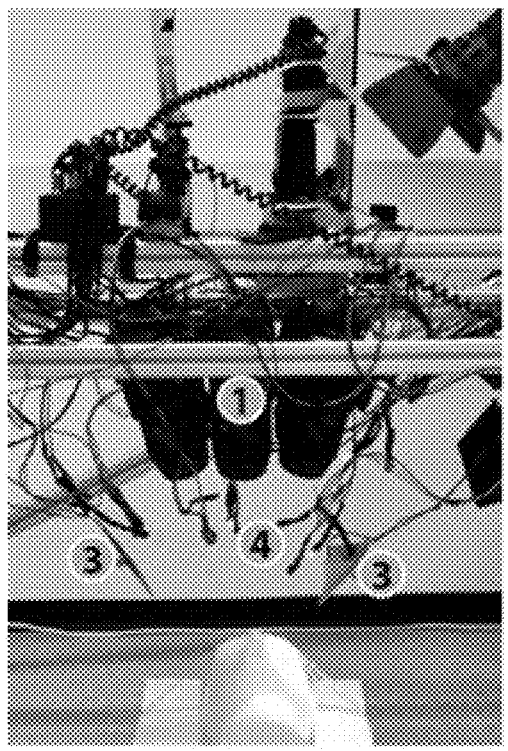
FIG. 4B illustrates a zoomed-in view of the example system for acquiring data used in an eye reconstruction technique, in accordance with an embodiment of the present invention.

FIG. 4A illustrates an example of a system 400 for acquiring data. FIG. 4B illustrates a zoomed-in view of certain components of the system 400. It should be appreciated that the system 400 may have a different number of certain components or may have other components than those depicted. Further, the embodiment shown in the figure is only one example of a data acquisition system 400 that may incorporate an embodiment of the invention. In some other embodiments, system 400 may have more or fewer components than shown in the figure, may combine two or more components, or may have a different configuration or arrangement of components.

The system 400 includes a camera array (1) including one or more cameras, a focused flash light (2), two lighting devices (3) used to control pupil dilation, and color lights (4) that produce highlights reflecting off of the cornea. The subject may be positioned on a headrest (5). The system 400 further includes one or more studio lamps (6) that are used during camera calibration. The lighting devices (3) may include high-power white light-emitting diodes (LEDs). The color lights may also include LEDs. The flash light (2) may include a modified flash for primary illumination. To help the subject remain still during acquisition, the setup is arranged such that the subject can lie on the floor with their head in the headrest (5), which may be situated under the camera array (1).

To obtain the best coverage in the space available, an appropriate number of cameras (e.g., three, four, five, six, or any other appropriate number) may be placed in a certain configuration, with a lens focused on the iris. As one example, the camera may include a Canon 650D camera with a 100 mm macro lens focused on the iris. Six cameras may be used in a 2 by 3 configuration. In some examples, the lens may be stepped down to f11 and the camera may be set to an ISO100 setting. In some examples, the exposure may be set according to the environment in which the images are captured. For example, the exposure may be set to 1 second in the event the images are captured in a dark room, and the flash (2) may provide the primary illumination. The main flash light (2) may include three elements, including a conventional flash (e.g., a Canon 600EX-RT), a cardboard aperture mask, and a lens. The assembly allows the system 400 to intensify and control the shape of the light so that reflections of the face and the eyelashes of the subject can be prevented as much as possible.

The color lights (4) may be used to show highlights on the cornea so that the transparent surface of the cornea can be visualized. In some embodiments, one or more white lights may be used to show one or more of the highlights. The color lights (4) may include an appropriate number of Red-Green-Blue (RGB) LEDs (e.g., two, three, four, five, six, seven, eight, nine, or any other appropriate number as needed) arranged in a specific pattern, or other appropriate type of lighting device. For example, the RGB LEDs may be arranged in a 3×3 pattern. In some embodiments, the RGB LEDs may be arranged such that similar colors are not adjacent to one another, in order to maximize the ability to uniquely detect the reflections of the LEDs on the cornea.

In some embodiments, pupil dilation is controlled with the lighting devices (3), which may include high-power white LEDs with adjustable brightness. The lighting devices (3) may be placed close to the eye that is not being captured. Because the pupil dilation of both eyes of the subject is linked, the dilation of the captured eye can be controlled indirectly by lighting the eye that is not being captured, avoiding an extra specular highlight on the captured eye. While two lighting devices (3) are shown in FIG. 4B, one of ordinary skill in the art will appreciate that one lighting device or more than two lighting devices may be used. In some embodiments, a focus pole with specifically marked distances may be placed in front of the subject to measure the captured eye focusing at different depths. The one or more studio lamps (6) may be used during camera calibration.

In some examples, the cameras of the camera array (1) may be calibrated using a calibration target. For example, a calibration target may include checkerboard of markers (e.g., CALTag markers). In some examples, a calibration target may be acquired in various positions throughout the capture volume (e.g., five, ten, fifteen, or any other appropriate number of positions). The positions of the color lights (4) (e.g., LED lights, or other appropriate lights) may be calibrated by imaging a mirrored sphere. The mirrored sphere may be placed at one or more locations in the scene at which the subject's eye is being captured, for example, close to a position at which the eye is located during acquisition. In some embodiments, the highlights of the color lights (4) on the mirrored sphere are detected in each captured image by first applying a Difference-of-Gaussian filter followed by a non-maximum suppression operator, resulting in single pixels marking the positions of the highlights. The detected highlight positions from a specific color light in the different cameras form rays that should all intersect at the 3D position of that color light after reflection on the mirrored sphere, which has a known radius (e.g., 5 mm, 10 mm, 15 mm, or any other appropriate radius). Accordingly, a nonlinear optimization problem can be formulated, with the residuals being the distances between the reflected rays and the position estimates of the color lights (4). The unknown color light and sphere positions may be solved using a nonlinear least-squares optimization algorithm (e.g. Gauss-Newton, Levenberg-Marquardt, steepest descent, conjugate gradient, or any other known nonlinear least-squares optimization).

To reconstruct as much of the visible eye as possible, the subject is directed to open their eyes very wide. Even with the eyes opened widely, much of the sclera is occluded in any single view. Because of this, a series of images are acquired that contain a variety of eye poses covering various possible gaze directions. For example, images may be acquired that include poses of the subject gazing straight, left, left-up, up, right-up, right, right-down, down, left-down, far-left, and far-right. The straight pose may be used as reference pose, as the straight pose neighbors all other poses except far-left and far-right.

A second series of images may then be acquired, this time varying the pupil dilation. The intricate geometry of the iris deforms non-rigidly as the iris dilator muscle contracts and expands to open and close the pupil. The dilation is subject-specific, thus different amounts of dilation for each subject is explicitly captured by gradually increasing the brightness of the lighting devices (3). For example, a series of ten images may be sufficient to capture the iris deformation parameterized by pupil dilation.

To initialize the eye capture reconstruction technique, partial reconstructions may be pre-computed for each eye gaze using a facial scanning technique. For example, a passive stereo system may be used to capture a 3D geometry of the subject's face, described in Beeler et al., *High-Quality Single-Shot Capture of Facial Geometry*, ACM Trans. Graphics (Proc. SIGGRAPH) 29, 40:1-40:9 (2010). Facial scanning techniques designed for skin may be used due to the sclera region of the eye being similarly diffuse as the skin, thus allowing partial sclera geometry to be obtainable using the skin facial scanning technique. The pre-computed per-gaze reconstructions may include reconstructed meshes for the eye at each eye gaze. As described below, the meshes may be used in later stages of the reconstruction technique. Additionally, the surrounding facial geometry that is visible may be used for providing context when rendering the eye.

Once the appropriate data is acquired or determined, the reconstruction technique may reconstruct the representation sclera representing the sclera part of the subject's eye. Reconstruction of the sclera is challenging because large parts are occluded by the eyelids and the eye socket at any given time. As previously indicated, the occlusion of portions of the sclera can be alleviated by acquiring images of the eye under multiple poses. As explained in further detail below, the different poses may be registered into a common frame and the partial scans or meshes may be integrated into a complete model of the eyeball.

Figure 5:
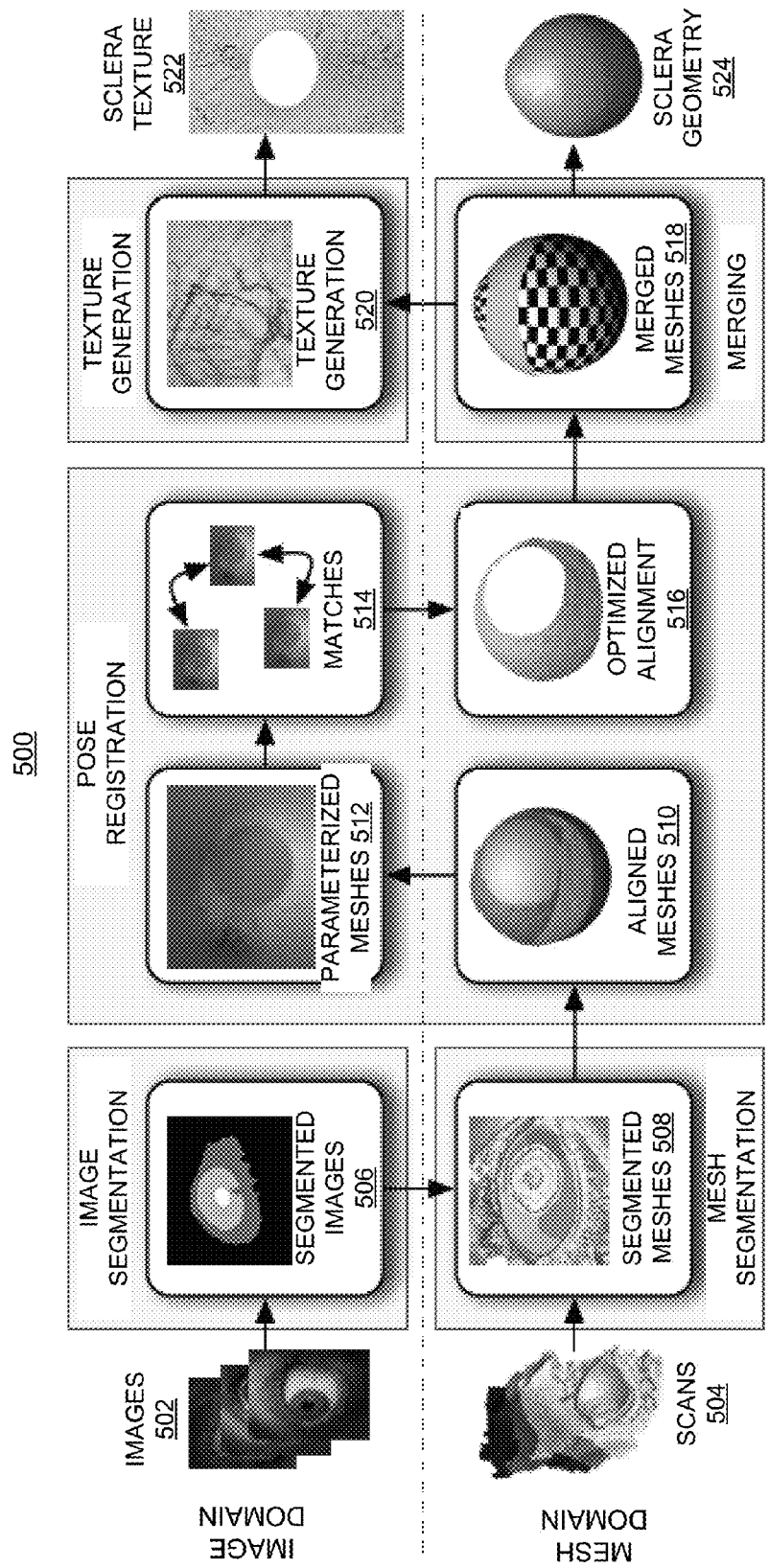
FIG. 5 illustrates an overview of a technique for reconstructing a sclera representation for a sclera part of an eye of a subject, in accordance with an embodiment of the present invention.

FIG. 5 illustrates an overview of a technique 500 for reconstructing a sclera representation for a sclera part of the subject's eye. The sclera reconstruction operates in both image and mesh domains. Input images 502 and meshes 504 are segmented to generate segmented images 506 and segmented meshes 508. The partial scans or meshes from the eye poses are registered using various pose registration processes, and are combined into a single model 524 of the sclera using a generic proxy eyeball. A high-resolution texture of the sclera is acquired using texture generation 520 and is extended via texture synthesis to generate a sclera texture 522. As described in more detail below, portions of the sclera are captured while the subject is gazing in different directions to reveal different portions of the sclera. Meshes of the portions of the sclera are generated, and the meshes are merged together to a single eye position. A single mesh is then generated to represent the entire eye by deforming a proxy eyeball mesh so that it fits the captured portions of the sclera.

Figure 6:
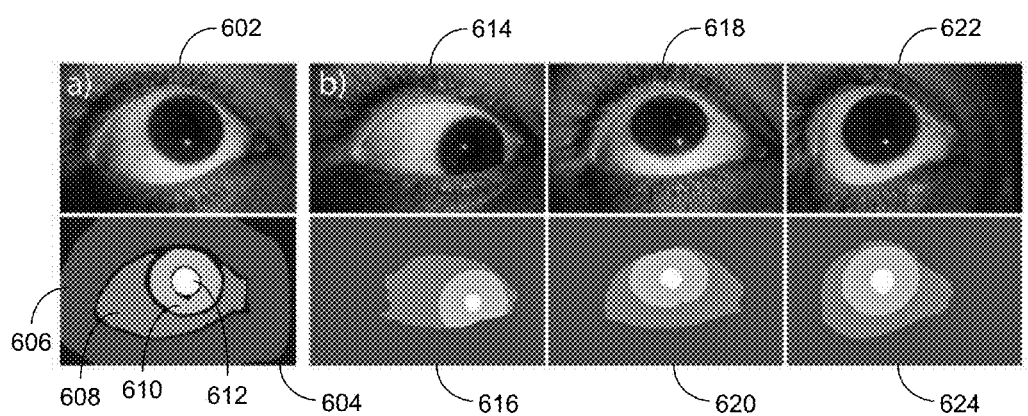
FIG. 6 illustrates an example of image segmentation, in accordance with an embodiment of the present invention.

The sclera reconstruction technique performs image segmentation for each acquired image to generate the segmented images 506. As previously described, the individual components of the eye require dedicated treatment, and thus the input images 502 are segmented to identify the skin part, the sclera part, the iris part, and the pupil part of the subject's eye. Numerous images may be acquired for a single eye dataset (e.g., 25 images, 50 images, 75 images, 100 images, 140 images, 150 images, or any other appropriate number), which includes all the different poses, the different pupil dilations, and the multiple cameras at different camera angles. As a result, manual segmentation would be quite tedious. Instead, a semi-supervised method is proposed to automate the segmentation process. All images may be captured under similar conditions, and thus the appearance of the individual parts or classes of the eye can be expected to remain similar. Because the classes are expected to remain similar, a nearest-neighbor classification may be employed to segment the images into the different classes. One or more of the images may be manually segmented into skin, sclera, iris and pupil parts. For example, as shown in FIG. 6, the image 602 may be manually segmented into a classification result 604 including a skin part 606, a sclera part 608, an iris part 610, and a pupil part 612. These manually segmented parts serve as examples, from which the nearest-neighbor classification algorithm may label the pixels of the other images automatically by assigning the label of the most similar example pixel. In some examples, similarity may be computed in a lifted 21-dimensional feature space of fifteen color and six Haralick texture features. This classification technique is fast since every pixel is treated independently. In some examples, high quality classification may be obtained by employing a post-processing step that uses topological rules specifying that the iris is the largest connected component of iris pixels, there is only a single pupil and the pupil is inside the iris, and the sclera part(s) are directly adjacent to the iris. FIG. 6 shows the final classification results 616, 620, and 624 for a subset of images 614, 618, and 622, respectively, based on the manually annotated example classification result 604. The classification results 604, 616, 620, and 624 may be used to create a mask for a particular part of the images. For example, a sclera mask may be created for the sclera part of the image. The mask may isolate the particular part of the image. In some embodiments, a manually classified image for an eye of one subject may be used to automatically classify images for an eye of another subject.

The sclera reconstruction technique may then perform mesh segmentation. For example, mesh segmentation may be obtained for each pose. Given the image-based classification, the geometry of the sclera may be extracted from the pre-computed initial mesh per-gaze reconstructions described above. For example, a sclera mask from the classification results 604, 616, 620, and 624 may be projected onto the corresponding pre-computed meshes of the different poses to get only the piece of the mesh that corresponds to the sclera. The projection may be done by transferring the sclera part of the classification results 604, 616, 620, and 624 from an image domain to a mesh domain. While the geometry of the sclera may be mostly accurate, the interface between the sclera and the iris and the interface between the sclera and the skin may contain artifacts or exhibit over-smoothing, both of which are unwanted properties. These unwanted properties may be removed. For example, while a single sphere only poorly approximates the shape of the eyeball globally (see FIGS. 19A-19B), locally the surface of the sclera may be approximated sufficiently well. Thus, the sclera mesh may be over-segmented into clusters of a certain size (e.g., 50 $mm^2$ or other appropriate size) using k-means. Further, a sphere with a certain radius (e.g., 12.5 mm radius, or other radius representing the average human eye) may be fit to each cluster. Vertices that do not conform with the estimated spheres may then be pruned, either in that they are too far off surface or their normal deviates strongly from the normal of the sphere. In some examples, a distance threshold of 0.3 mm and normal threshold of ten degrees may be used, which empirically provides good results in practice. The steps of clustering, sphere fitting, and pruning may be iterated until convergence. In some examples, convergence may be reached in less than five iterations. Once convergence is reached, a resulting set of partial sclera meshes is obtained, including one sclera mesh for each captured gaze direction.

Based on the image and mesh segmentation, a sclera mesh is obtained for each pose. The sclera meshes may have a random orientation because the poses are captured with different gaze directions and slightly different head positions due to the difficulty for the subject to remain completely still during data acquisition. As a result, the relationship between the different poses is unknown. The sclera reconstruction technique may thus perform pose registration to align the poses to each other. To combine the partial sclera meshes into a single model, a rigid transformation of the meshes with respect to a reference pose may be recovered. An optical flow technique may be used to compute dense pairwise correspondences in order to align the partial sclera meshes. An example of optical flow is described in Brox et al., *High Accuracy Optical Flow Estimation Based on a Theory for Warping*, ECCV, Springer, 25-36 (2004). For example, using two images as input, an optical flow algorithm may find dense correspondences from the first image to the second image. Therefore, the flow from one camera image to another camera image may be computed. If it is known where a feature point on the sclera projects in the first image, it can then be computed where the feature point projects in the second image based on the optical flow result calculated for the two images. Therefore, optical flow may be used to find correspondences of sclera features between the different captured images. Optical flow is an image-based technique and may be reliable only on small displacements. As such, the poses may be aligned first using the gaze direction and then the individual meshes may be parameterized jointly to a uv-plane. The correspondences provided by the optical flow are then employed to compute rigid transformations of the individual meshes with respect to the reference pose. These steps are iterated until convergence is reached. In some examples, convergence may be reached in 4-5 iterations.

Pose registration may begin with initial alignment to obtain aligned meshes 510. Because the subject's head does not remain still during data acquisition, a sphere may be used to estimate an approximate position of the eye for each pose. The pose transformations are estimated by fitting the sphere to the reference mesh and aligning all other meshes so that their gaze directions match. The gaze direction is estimated for every pose using the segmented pupil. The segmented pupil mask may be projected onto the meshes, which provides an estimate for the gaze directions. The gaze directions from the different poses may then be aligned to get an initial alignment. After initial alignment, joint parameterization is performed to obtain parameterized meshes 512. Textures are generated for the meshes of the different poses, and the textures need to have a joint parameterization. The aligned meshes 510 are parameterized to a common uv-space using spherical coordinates. Given the uv-parameterization, textures for the individual poses may be computed by projecting the poses onto the image of the camera that is closest to the line of sight of the original pose. This naive texturing approach is sufficient for pose registration, and reduces view-dependent effects that could adversely impact the matching. Correspondence matching may then be conducted to obtain matches 514 between correspondences in textured space to find the same points in textures of different meshes. Thus, the textures are used to find matching correspondences. For example, the optical flow of the individual sclera textures may be computed using only the blue channel of the red, green, and blue channels of the images. The blue channel may be used because it offers the highest contrast between the veins and the white of the sclera. The resulting flow field may then be sub-sampled to extract 3D correspondence constraints between any two neighboring sclera meshes. Only constraints that are both well localized and well matched may be extracted. Matching quality is assessed using the normalized cross-correlation (NCC) within a k×k patch. Localization is directly related to the spatial frequency content present within this patch, quantified by the standard deviation (SD) of the intensity values. In some embodiments, the parameters may be set such that k=21 pixels, NCC>0, and SD<0.015. One of ordinary skill in the art will appreciate that other appropriate parameter values may be used. Optimization may then be performed to achieve optimized alignment 516 between the poses. For example, once the correspondences are obtained, the orientations of the poses may be optimized so that the correspondences geometrically are as close as possible. Optimization may include jointly optimizing the rigid transformations of all the poses using a nonlinear least-squares optimizer (e.g. Gauss-Newton, Levenberg-Marquardt, steepest descent, conjugate gradient, or any other known nonlinear least-squares optimization) so that the weighted squared distances between the correspondences are minimized. The weights reflect the local rigidity of the detected correspondences and are computed from Euclidean residuals that remain when aligning a correspondence plus its five neighbors rigidly. In some examples, the optimization may be followed by a single iterative-closest-points (ICP) iteration to minimize the perpendicular distances between all the meshes.

Once pose registration is complete, the sclera meshes of the different poses are aligned. The sclera reconstruction technique may then perform a sclera merging process to merge the sclera meshes and obtain a merged mesh 518. For example, after registering all partial scans or meshes of the sclera, the partial scans are combined into a single model of the eye. The sclera merging process uses a generic eyeball proxy mesh and the aligned sclera meshes as inputs. The generic eyeball proxy mesh includes an average shape of a human eyeball, and is used to provide a mesh for the back of the eye, which was occluded during data acquisition. The generic eyeball proxy mesh is fit to the aligned meshes, and the meshes (the partial scans) are merged into a single mesh. The single mesh is then combined with the eyeball proxy mesh to complete the missing back of the eyeball.

The proxy fitting phase of the sclera merging process includes an optimization to change the dimensions of the proxy to fit it to the sclera meshes as closely as possible. A goal of the optimization is to minimize the square distances between the proxy mesh and all the other sclera meshes so that the proxy fits the sclera meshes as tightly as possible. In some embodiments, a nonlinear least-squares optimization algorithm (e.g. Gauss-Newton, Levenberg-Marquardt, steepest descent, conjugate gradient, or any other known nonlinear least-squares optimization) may be used to minimize distances between the proxy mesh and the sclera meshes. In some examples, a two-step optimization is done using the optimization algorithm because the anatomy of the face leads to less of the sclera being recovered in the vertical direction, resulting in the vertical shape being less constrained. In the first step, the process optimizes for uniform scaling. In the second step, the process optimizes for horizontal scaling. In both steps, the process optimizes for translation and rotation of the eyeball while keeping the rotation around the optical axis fixed. As a result of the proxy fitting, the sclera meshes and the proxy mesh are aligned.

Once the sclera meshes and the proxy mesh are aligned, a single mesh representing the eyeball is obtained by performing sclera merging and eyeball merging. With respect to sclera merging, the eyeball proxy geometry prescribes the topology of the eyeball. For every vertex of the proxy eyeball, a ray is cast along its normal and intersected with all sclera meshes. The weighted average position of all intersections along this ray is considered to be the target position for a vertex. The determined target positions indicate a position at which each vertex is to be adjusted along its normal direction (if needed) in accordance with the weighted averages so that the proxy mesh has the same details as that of the actual eye of the subject. The standard deviation of the intersections may be used as a confidence measure. The weights are a function of the distance of the intersection to the border of the mesh patch and provide continuity in the contributions. The sclera merging only deforms the proxy eyeball mesh where scan data is available, thus eyeball merging is performed to obtain the portion of the mesh corresponding to the remaining portion of the eyeball. To ensure a smooth eyeball, the deformation of the proxy eyeball mesh to the sclera mesh is propagated to the back of the eyeball using a deformation framework, such as a Laplacian deformation. Such a deformation framework is described in Sorkine et al., *Laplacian Surface Editing*, In Proc. SGP, 175-184 (2004). The target weighted-average vertex positions and confidence measures found in the sclera merging step are included as weighted soft-constraints. The result of the sclera merging process is a single eyeball mesh that fits the captured sclera regions including the fine scale details and surface variation of the actual sclera part of the subject's eye, and also smoothly completes the back of the eye.

To complete the sclera reconstruction, a sclera texturing process may be performed to build a complete texture space for the subject's eye. A texture image is generated, and the texture image can be filled from the captured images of the different eye poses. A color may be computed for each point on the reconstructed sclera surface using a texture mapping approach that project the 3D object mesh onto multiple camera images. All images for all eye poses are considered and the computed sclera segmentation is used to identify occlusion. One approach is to naively choose the most front-facing viewpoint for each surface point, however this approach may leads to visible seams when switching between views. Such seams may be avoided by averaging over all views, but this may lead to texture blurring. Another approach may include solving the Poisson equation to combine patches from different views while enforcing the gradient between patches to be zero. This approach may lead to strong artifacts when neighboring pixels at the seam have high gradients, a situation that may occur due to the high contrast of a red blood vessel and white sclera. Yet another approach may include separating the high and low frequency content of the images, and then applying the Poisson patch combination approach only for the low frequency information, which has low gradients. The naive front-facing viewpoint approach may then be used for the high frequencies, where seams are less noticeable because most seams come from shading differences and the shading on a smooth eye is low-frequency by nature. After texture mapping, the frequencies are recombined.

Figure 7:
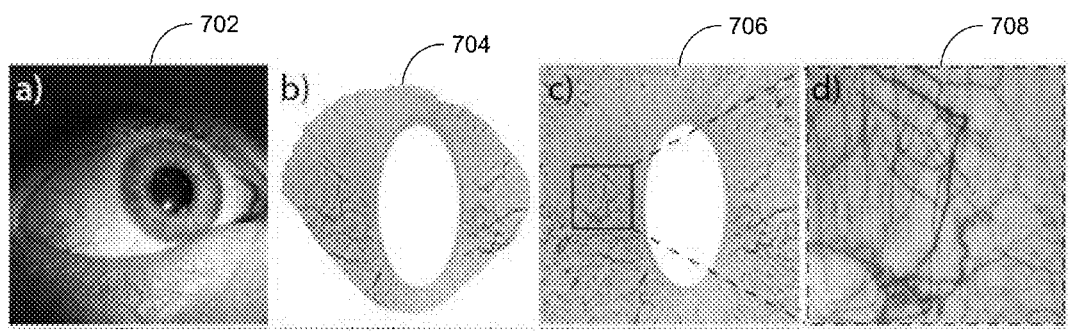
FIG. 7 illustrates an example of sclera texturing, in accordance with an embodiment of the present invention.

FIG. 7 illustrates an image 702 of an eye of a subject and a computed texture map 704 for the eye. The sclera is textured from multiple views of multiple different eye poses. The resulting texture map 704 for the eye contains all the visible parts of the sclera. The sclera texturing process computes a color for each point that was seen by at least one camera, but the occluded points will remain colorless. Depending on the intended application of the eye reconstruction, it is possible that texture at additional regions of the sclera may be required, for example if an artist poses the eye into an extreme gaze direction that reveals part of the sclera that was never observed during capture. Accordingly, the sclera texture map may be synthetically completed using texture synthesis. An example of an appropriate texture synthesis method is described in Efros and Leung, *Texture Synthesis by Non-Parametric Sampling*, IEEE ICCV, 1033-1038 (1999).

Figure 8:
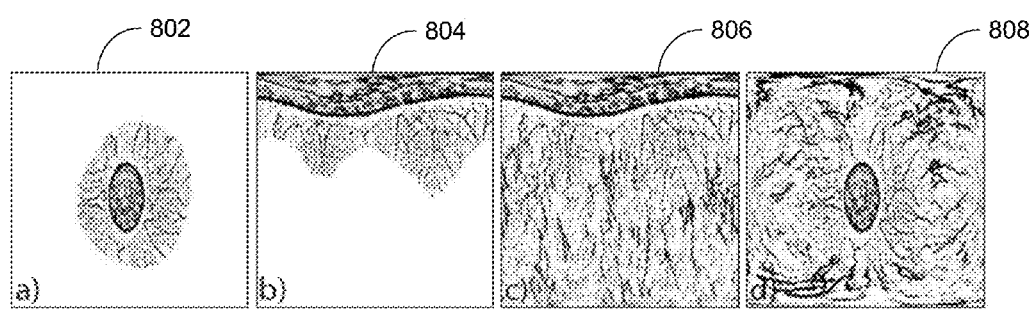
FIG. 8 illustrates an example of sclera texture synthesis, in accordance with one embodiment of the present invention.

Consistency of blood vessels is desired, which should naturally continue from the iris towards the back of the eye. This can be accomplished by performing synthesis in Polar coordinates, where most veins traverse consistently in a vertical direction, and the synthesis can be seeded with a few vertical vein samples. FIG. 8 illustrates an example of sclera texture synthesis using rotated synthesis. As illustrated in FIG. 8, the texture map is transformed or re-parameterized from Cartesian coordinates in frame 802 to Polar coordinates in frames 804 and 806 such that the iris is located at the top (north pole) of the frames 804 and 806. Texture synthesis is then performed in Polar coordinates. The texture synthesis is shown in frame 806 with the veins being synthesized down toward the bottom of the frame 806. Texture synthesis is performed in a way that preserves vein orientation, as shown in frame 806. The final texture is rotated back to Cartesian coordinates in frame 808. In some embodiments, texture synthesis is performed on the high frequency information in order to complete the texture. The rotated synthesis may be performed only on the high frequencies in order to avoid synthesized shading artifacts. Corresponding low-frequency content may be created by smooth extrapolation of the computed low-frequency texture.

Missing surface details can also be synthesized in the back of the eye using the same texture synthesis approach, but instead operating on a displacement map. The displacement map may be computed as the difference between the original and a smoothed version of the reconstructed eyeball. The final result is a complete eyeball with continuous texture and displacement at all points. A complete texture region 706 and a zoom region 708 are shown in FIG. 7.

Once the sclera representation is reconstructed for the sclera part of the subject's eye, a representation of the transparent cornea may be reconstructed. Although the cornea includes several thin layers with different optical properties, it sufficient to model the cornea as a single surface with a single medium and a single index of refraction inside the eye. A surface optimization method may be used that aims to satisfy constraints from features that are either reflected off or refracted through the cornea.

Figure 9A:
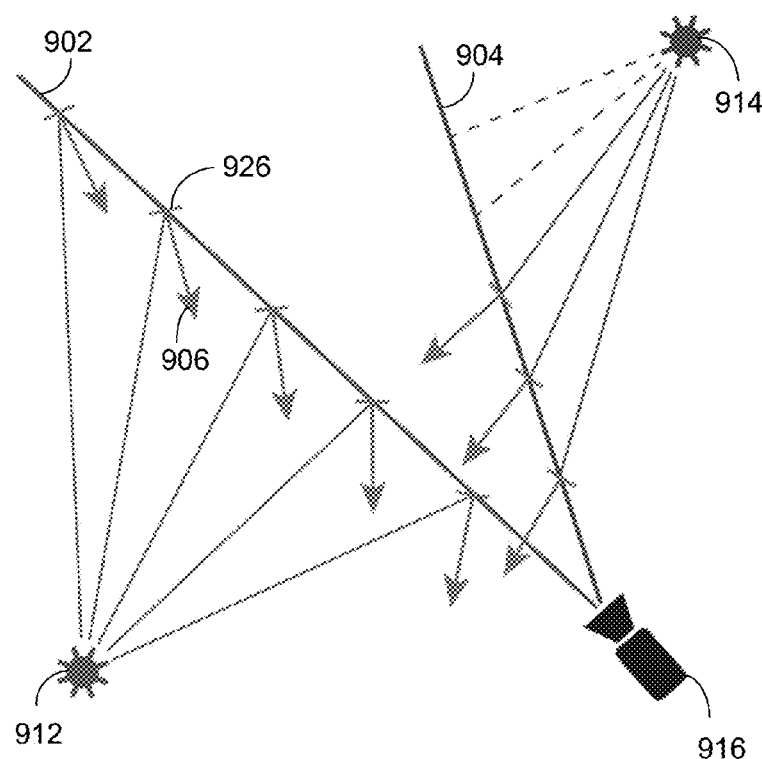
FIG. 9A illustrates an example of depth and normal ambiguity of a highlight, in accordance with one embodiment of the present invention.
Figure 9B:
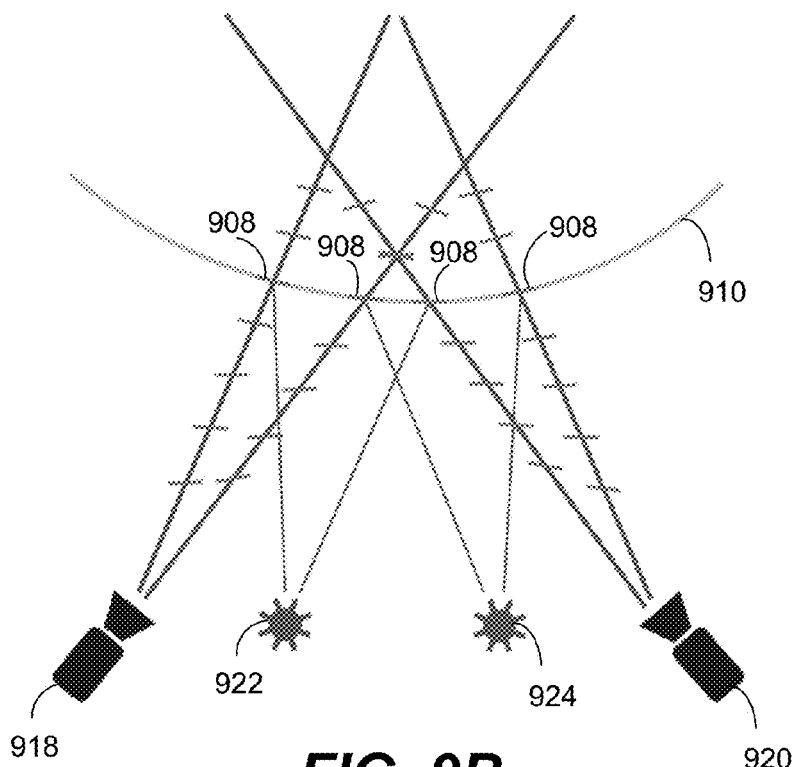
FIG. 9B illustrates an example of a sparse normal field in a multi-view setting, in accordance with one embodiment of the present invention.

Reconstructing transparent surfaces requires different approaches than diffuse surface reconstruction since a transparent surface is not directly visible. Transparent surfaces are generally not completely transmissive, but a fraction of light is reflected if the refractive indices of the media involved differ. Thus, a bright light placed in front of the cornea will cause a visible highlight that provides a cue about the surface. However, the position of the highlight is view-dependent and cannot directly be used in a multi-view setting. For a single-view setting, there is an ambiguity between the depth along the viewing ray corresponding to a highlight and the normal of the surface. The theory behind reconstruction of transparent surfaces using the techniques described herein is described with respect to FIGS. 9A and 9B. FIG. 9A illustrates an example of depth and normal ambiguity of a highlight using a single view from camera 916 and multiple lights 912, 914. FIG. 9B illustrates an example of a sparse normal field in a multi-view setting with multiple cameras 918, 920 and multiple lights 922, 924. For every position along a viewing ray 902 or 904, there exists a surface tangent 926 and a surface normal 906 reflecting the ray to the origin of the light. The viewing ray 902 and 904 is the ray along which the highlights are seen in an image. The reflected ray is shown by viewing ray 902 from camera 916 with respect to light 912. This phenomenon creates a surface normal field defined by all possible viewing ray direction and depth combinations. A similar surface normal field is produced from refractions. The refracted ray is shown by viewing ray 904 from camera 916 with respect to light 914. The reflection and refraction surface normal fields and surface tangents of different views only coincide at positions 908 of the actual surface 910, as illustrated in FIG. 9B. This property may be used to reconstruct the cornea.

Due to the use of a limited number of lights to produce highlights on the cornea (e.g., LED lights (4) in FIG. 4B), only a sparse sampling of the normal fields may be produced. As a result, regularization needs to be added to ensure a unique solution. Regularization may be provided through the chosen surface representation. For example, an open uniform B-spline surface with an appropriate number control points may be used (e.g., 10, 25, 50, 100, 125, 150, 200, or other appropriate number). The uniform B-spline surface has more representation power than a 4th order Zernike polynomials, but can be controlled locally, which is beneficial for optimization. The control points may be spaced regularly and initialized to the surface of the eyeball proxy mesh described above with respect to the sclera merging process. The position of the boundary control points are optimized such that the surface boundaries fit the proxy geometry. In some examples, the boundary control points are kept fixed and are not part of the surface optimization described below.

The surface of the cornea is optimized using three different types of constraints. The constraints include reflection constraints, refraction constraints, and position constraints. The constraints are determined using different pieces of information that are available. One piece of available information is the previous reconstruction of the sclera. It is known that the cornea is an extension of the sclera in that the sclera turns into the cornea at the sclera boundary. The position constraints can be determined based on this known feature of the sclera and cornea. Another piece of information that is available is the reflection of the color lights (e.g., color lights (4) in FIG. 4B) off of the cornea surface. The reflection constraints can be obtained using these reflections. Yet another piece of information that is available is the refracted light from the color lights that appears behind the cornea surface that can be seen from the cameras. The refraction constraints can be obtained from the refracted light. The different constraints are described in more detail below. The goal of the optimization is to minimize these constraints. For example, the optimization may minimize the distance of the surface of the cornea to a position constraint. For the refraction constraints, the optimization may minimize the distance between the refracted ray and the actual ray formed by a light source and the surface. For the reflection constraint, the optimization may minimize the mismatch between the surface normal and the required reflection normal so that the light will be reflected into the camera at the correct position.

Reflection constraints may be computed by detecting highlights in the captured images. For example, the calibrated lights (e.g., color lights (4), such as nine LEDs, or other appropriate number of lights) placed in front of the cornea are imaged as highlights in the different camera views. From these highlights, the reflection constraints can be extracted, which prescribe the normal for any point along the viewing ray through the highlight. Because the cornea is convex, every light-view pair contributes one constraint, assuming the reflection of the light is visible in the camera view. In addition, because the different poses are aligned in the pose registration described above, constraints from different poses can be combined. The highlights are detected and identified similarly as in the calibration of the cameras described above. While the highlights in the calibration images are acquired in complete darkness, the highlights now appear superimposed on the iris in the input images, which can lead to false positive detections. These unwanted detections may be removed by fitting a 2D Gaussian curve to intensity profiles of all the highlight candidates to determine their width. Because the highlights have a constant size, false positives can be removed with a lower (e.g., 3px) and upper (e.g., 15px) threshold on the standard deviation of the Gaussian.

Conceptually, refraction constraints are similar to reflection constraints. Instead of observing the reflected highlight of a known light, the refraction of a feature on the iris at an unknown position may be observed. Furthermore, the angle of refraction depends on a refractive index. Both the position of the feature and the refractive index are included as unknowns in the optimization and are solved for. A feature point on the iris contributes one refractive constraint per view. The corresponding image location in the different views may be estimated using optical flow. Optical flow may be used to find correspondences of iris features between the different captured images. For example, an optical flow algorithm with two input images may find dense correspondences from the first image to the second image. The flow from one camera image to another camera image may be computed. If it is known where a feature point on the iris projects in the first image, it can then be computed where the feature point projects in the second image based on the optical flow result calculated for the two images. Therefore, optical flow may be used to find correspondences of iris features between the different captured images. A set of rays from the images should all intersect at a same point (see $P^{iris}$ 1006 in FIG. 10A below). Features are filtered as described in the correspondence matching of the sclera reconstruction described above, for example, using NCC>0.6 and SD<0.02. Similar as that described above for reflection constraints, refraction constraints can be combined from all poses. The distribution density of the features varies substantially, as there are not any in the pupil, for example. To account for the variation of the distribution density of the features, the constraints may be weighed by the local density, approximated by the distance d to the 10th nearest constraint as $w^{refr}=NCC/d^2$, where NCC is the average normalized cross correlation score between corresponding image patches used as a measurement of the quality of the constraint.

Position constraints are one or more points extracted from the merged sclera mesh generated using the sclera merging process described above. The position constraints should include points that are within the transition region between the sclera and the cornea. The purpose of the position constraints is to provide a continuous transition from the cornea to the sclera. Position constraints are randomly sampled on the sclera in the vicinity of the corneal boundary. To ensure a good distribution, the position constraints should include a sparse sampling of the available points on the sclera mesh. For example, constraints that are closer than a certain distance to each other are rejected (e.g., 0.5 mm, 1 mm, 1.5 mm, 2 mm, or any other appropriate distance).

Figure 10A:
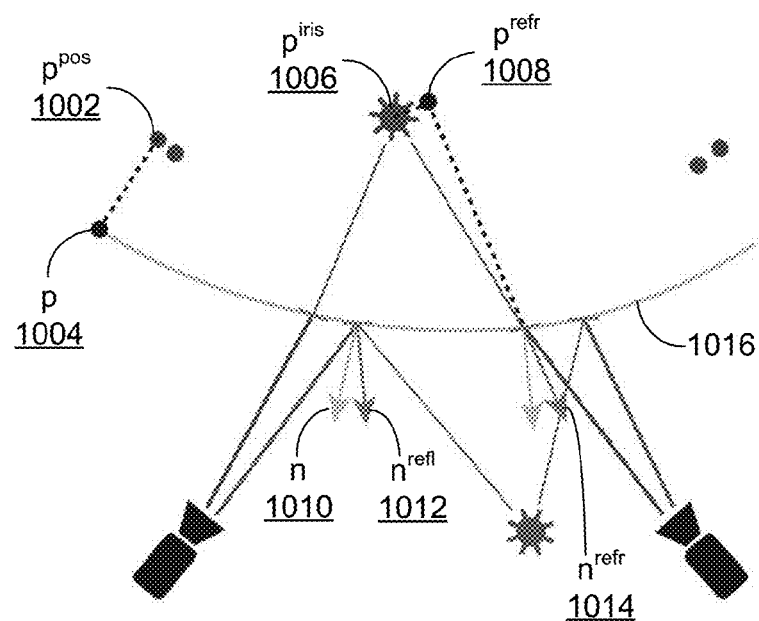
FIG. 10A illustrates an example of corneal constraints before optimization, in accordance with one embodiment of the present invention.
Figure 10B:
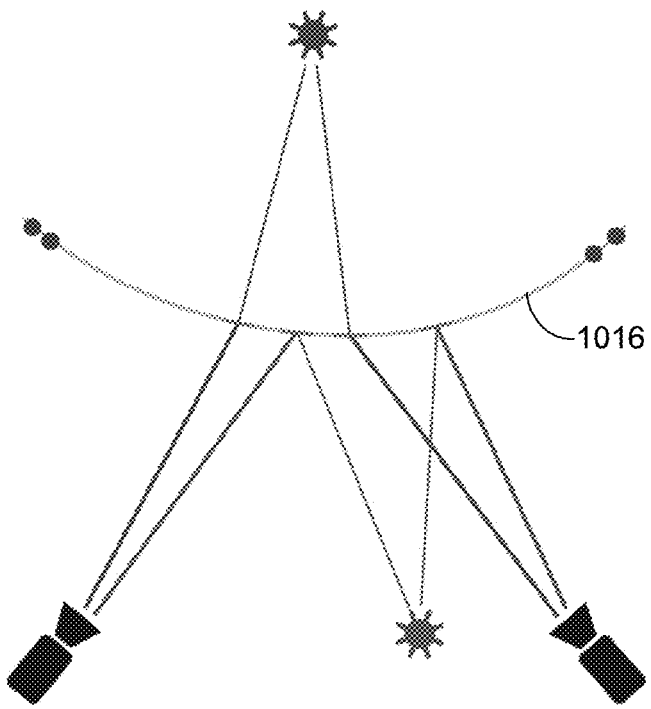
FIG. 10B illustrates an example of a corneal surface after optimization, in accordance with one embodiment of the present invention.

FIG. 10A illustrates examples of various constraints and a corneal surface 1016. The term $p^{pos}$ 1002 is a position constraint. As noted above, the $p^{pos}$ 1002 position constraint is a point that may be extracted from the merged sclera mesh. The $p^{pos}$ 1002 position constraint represents a position that is not on the actual cornea of the subject, but which is on the boundary between the sclera and the cornea. The optimization uses the $p^{pos}$ 1002 position constraint because the surface of the cornea would ideally go through this point to create a realistic model of the subject's cornea. The term p 1004 is the position on the corneal surface 1016 that is closest to the $p^{pos}$ 1002 position constraint. The term $n^1$ 1010 is the surface normal vector of the surface at the intersection point of the ray coming from the camera 1018. The term $n^{refl}$ 1012 is a reflection normal, which is the normal that is required so that the light from light 1020 is reflected at that position into the camera 1018. Thus, the reflection normal $n^{refl}$ 1012 is a virtual normal that is the target normal, and the goal of the optimization is to have the surface normal $n^1$ 1010 match the reflection normal $n^{refl}$ 1012. The term $p^{iris}$ 1006 is an estimated point on the iris. For example, $p^{iris}$ 1006 may be estimated using correspondences determined using optical flow techniques, as described above. The term $p^{refr}$ 1008 is a point close to $p^{iris}$ 1006. For example, if the ray 1024 from the camera 1022 intersects the surface 1016 and is refracted at the surface normal $n^2$ 1026, the ray 1024 will end up at $p^{refr}$ 1008. The point $p^{refe}$ 1008 is the closest point on that ray to $p^{iris}$ 1006. The point $p^{refr}$ 1008 may be determined based on an index of refraction corresponding to the medium behind the surface 1016. The index of refraction is first initialized based on a user-provided estimation. The index of refraction is then calculated as part of the non-linear optimization described below. The term $n^{refr}$ 1014 is a refraction normal, which is the normal that is required so that visualization of the point $p^{iris}$ 1006 is refracted at that position into the camera 1022. The refraction normal $d^{refr}$ 1014 is a virtual normal that is the target normal, and the goal of the optimization is to have the surface normal $n^2$ 1026 match the refraction normal $n^{refr}$ 1014. FIG. 10B illustrates the corneal surface 1016 once optimization is performed and the constraints are satisfied.

With a given set of reflection, refraction, and position constraints (such as those illustrated in FIG. 10A), and an initial guess of the corneal surface (such as corneal surface 1016 in FIG. 10A before optimization), the surface of the cornea can be reconstructed. To reconstruct the cornea, various unknown parameters related to the cornea are optimized with a two stage approach. In particular, the corneal reconstruction technique optimizes the control points of the surface representation (e.g., a B-Spline surface), a refractive index, and the unknown positions of the feature points on the iris which are used for the refraction constraints. The optimization may include a non-linear optimization that is solved using a nonlinear optimization algorithm (e.g. Gauss-Newton, Levenberg-Marquardt, steepest descent, conjugate gradient, or any other known nonlinear optimization) by minimizing the error:

$$E^{tot}=\lambda_{pos}E^{pos}+\lambda^{refl}E^{refl}+\lambda^{refr}E^{refr}, \quad (1)$$

where $\lambda^{pos}=0.1$, $\lambda^{refl}=1$, and $\lambda^{refr}=1$ are user-defined weight parameters. One of ordinary skill in the art will appreciate that other values for $\lambda^{pos}$, $\lambda^{refl}$, and $\lambda^{refl}$ may be used. The $\lambda$ weight parameter can be increased for a given constraint to give more weight to that constraint. In some examples, if it is determined that it is more important that the reflection and refraction constraints are satisfied, then the reflection and refraction constraint terms $E^{refl}$ and $E^{refr}$ be weighted more heavily than the position constraint $EP^{pos}$.

The error for the position constraints is given as:

$$E^{pos}=\frac{1}{|P|}\sum_{i \in P}\|p_i - p_i^{pos}\|^2, \quad (2)$$

where $p^{pos}$ denotes the position of the constraint and p is the nearest point on the corneal surface to $p^{pos}$. The term $1/|P|$ is a normalization term. The equation (2) represents the sum of the difference between p and $p^{pos}$ for all of the individual points that were extracted from the merged sclera mesh. The term $p_i$ minus $P_i^{pos}$ indicates the distance from each position constraint to a corresponding closest point on the cornea. The optimization equation (2) operates to minimize the distances.

The error for the reflection constraints Q is given as:

$$E^{refl} = \frac{1}{|Q|} \sum_{i \in Q} \|n_i - n_i^{refl}\|^2, \qquad (3)$$

where n is the current surface normal and $n^{refl}$ is the targeted surface normal. The term $1/|Q|$ is a normalization term. The equation (3) represents the sum over the reflection constraints. For example, the equation (3) sums over all the highlights extracted from the captured images. As previously described, $n_i$ are the actual normals and $n_i^{refl}$ are the reflection normals extracted from the highlights. The optimization equation (3) operates to minimize the mismatch between the two normals $n_i$ and $n_i^{refl}$.

The error for the refraction constraints R is given as:

$$E^{refr} = \frac{1}{|R|} \sum_{i \in R} w_i^{refr} \|p_i^{iris} - p_i^{refr}\|^2, \qquad (4)$$

where $p^{iris}$ is the point on the iris, $p^{ref}$ the closest point on the refracted ray and $w^{refr}$ is its corresponding weight. The term $1/|R|$ is a normalization term. Optimizing the distance to the closest point has proven to be more stable than optimizing the mismatch of the normals analogously to Equation (3). The equation (4) represents the sum over the refraction constraints. As previously described, $p_i^{iris}$ are points on the iris and $p_i^{iris}$ are the closest points on a ray to $p^{iris}$. The optimization equation (4) operates to minimize the mismatch between the two points $p_i^{iris}$ and $p_i^{refr}$.

In the first step of the two-stage approach, the optimization optimizes the control point positions of the surface representation (e.g., the B-Spline surface). In some examples, the control point positions are optimized only along the optical axis of the eye and the boundary control points are kept fixed at all times. After convergence, the surface is kept fixed and the second step includes optimizing for the refraction constraint points on the iris ($p^{iris}$) and the refractive index. Iteration is performed by alternating the two steps until the overall improvement drops below $10e^{-10}$.

Figure 11A:
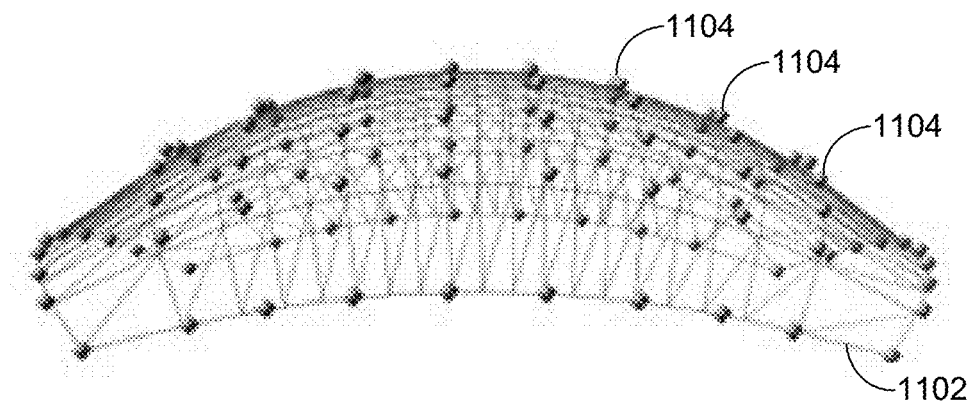
FIG. 11A illustrates an example of B-spline control points on an initial surface, in accordance with one embodiment of the present invention.
Figure 11B:
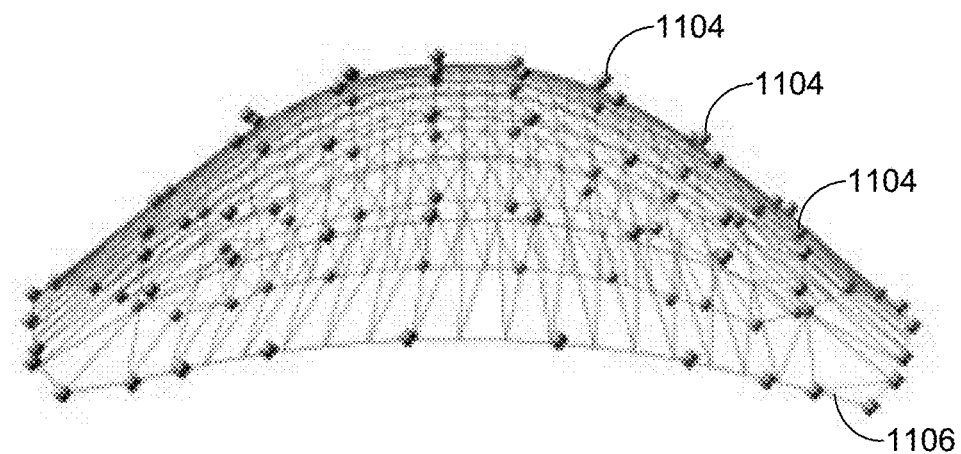
FIG. 11B illustrates an example of B-spline control points on an optimized surface, in accordance with one embodiment of the present invention.
Figure 12A:
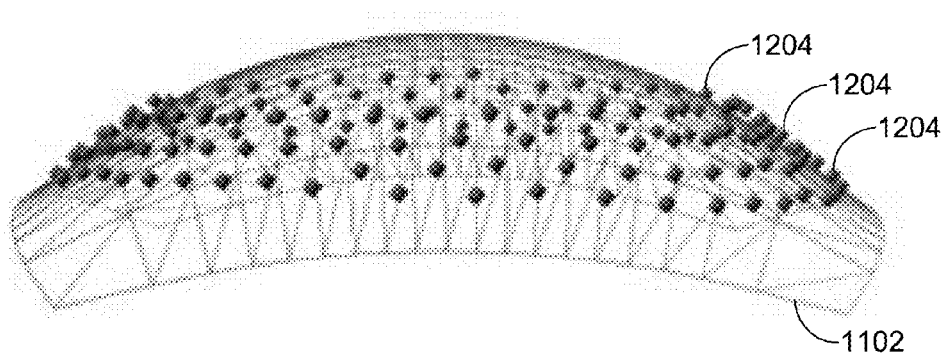
FIG. 12A illustrates an example of position constraints on an initial surface, in accordance with one embodiment of the present invention.
Figure 12B:
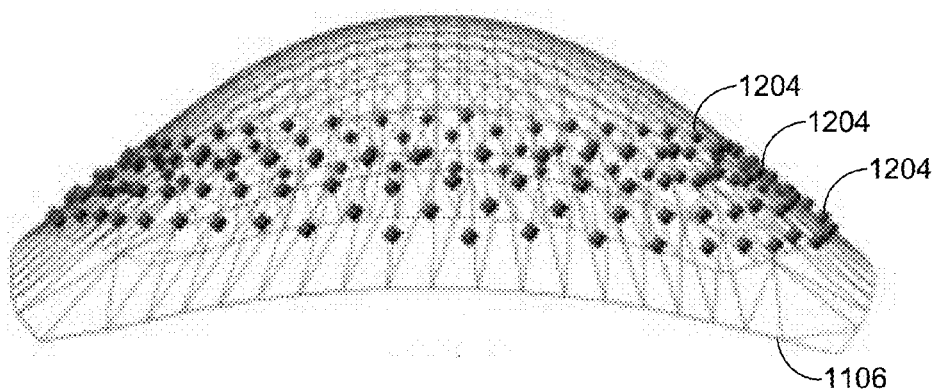
FIG. 12B illustrates an example of position constraints on an optimized surface, in accordance with one embodiment of the present invention.
Figure 13A:
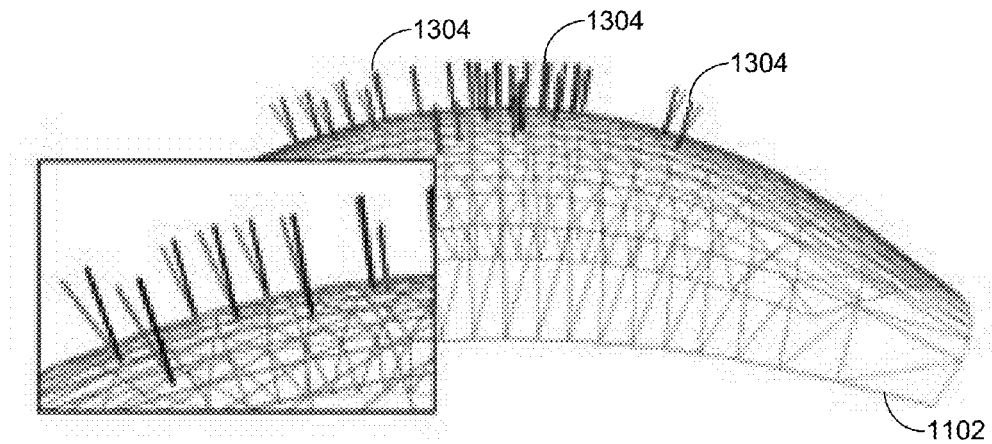
FIG. 13A illustrates an example of a subset of reflection constraints on an initial surface, in accordance with one embodiment of the present invention.
Figure 13B:
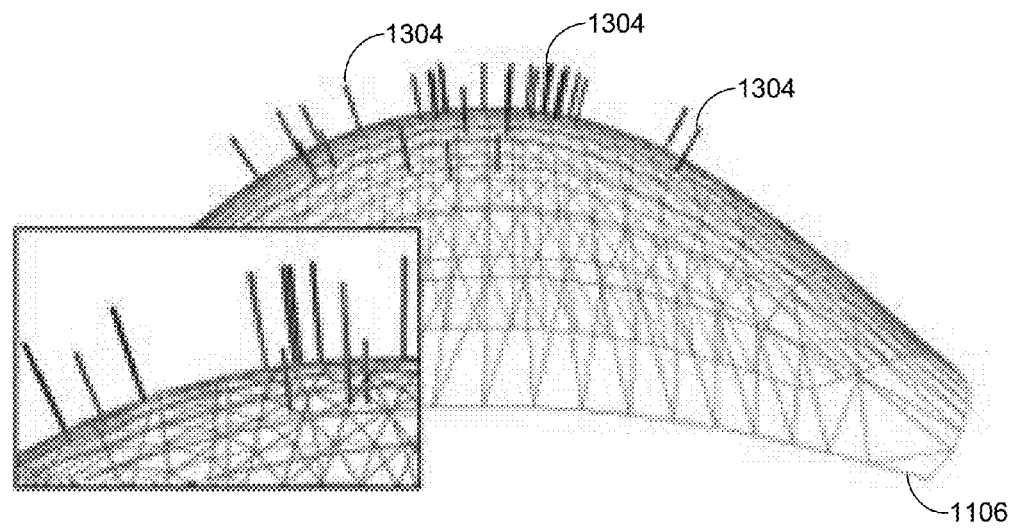
FIG. 13B illustrates an example of a subset of reflection constraints on an optimized surface, in accordance with one embodiment of the present invention.
Figure 14A:
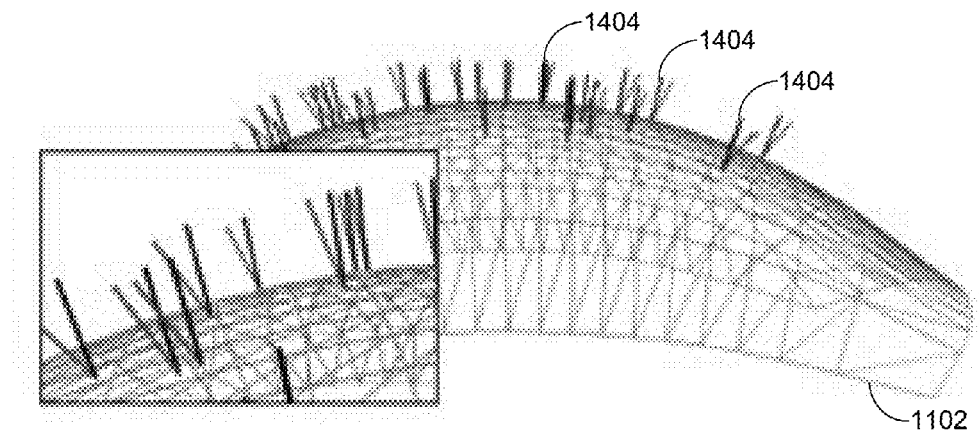
FIG. 14A illustrates an example of a subset of refraction constraints on an initial surface, in accordance with one embodiment of the present invention.
Figure 14B:
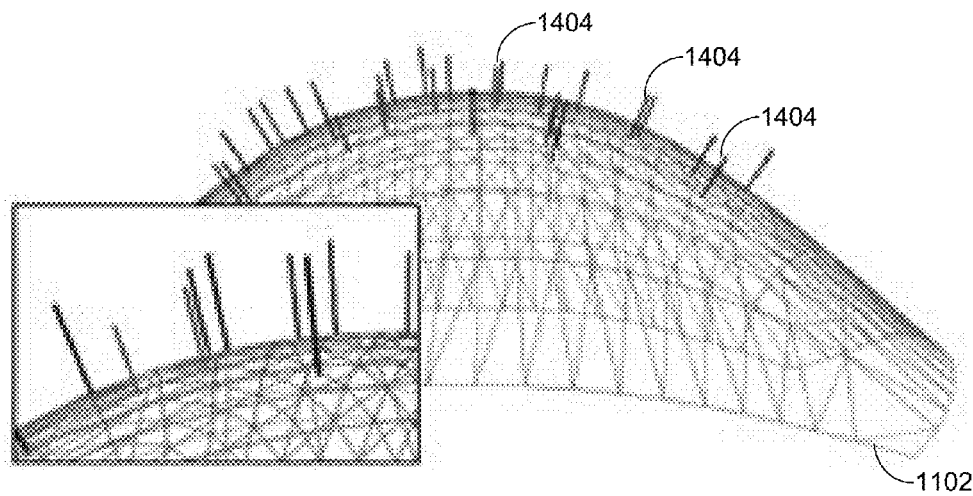
FIG. 14B illustrates an example of a subset of refraction constraints on an optimized surface, in accordance with one embodiment of the present invention.

FIGS. 11A, 11B, 12A, 12B, 13A, 13B, 14A, and 14B illustrate an initial corneal surface 1102, an optimized corneal surface 1106, and various constraints for one dataset. For example, FIG. 11A illustrates the initial corneal surface 1102 and the surface representation control points 1104. FIG. 11B illustrates the optimized corneal surface 1106 and the surface representation control points 1104. FIG. 12A illustrates the initial corneal surface 1102 and the position constraints 1204. FIG. 12B illustrates the optimized corneal surface 1106 and the position constraints 1204. FIG. 13A illustrates the initial corneal surface 1102 and the reflection constraints 1304. FIG. 13B illustrates the optimized corneal surface 1106 and the reflection constraints 1304. FIG. 14A illustrates the initial corneal surface 1102 and the refraction constraints 1404. FIG. 14B illustrates the optimized corneal surface 1106 and the refraction constraints 1404.

Once the cornea part of the eye is reconstructed by optimizing the optimized corneal surface representation (e.g., the B-Spline surface), the eyeball mesh may be updated with the optimized cornea by smoothly blending the corneal surface representation into the eyeball mesh. As a result, a single mesh is formed with the corneal surface representation and the eyeball mesh merged together. For example, corneal samples may be computed for each eyeball vertex by intersecting the cornea in the direction of eyeball normals. The iris masks (e.g., from the classification results 604, 616, 620, and 624 described above) may then be dilated, blurred, projected onto the cornea, and averaged to compute blending weights. The eyeball vertices may then be combined with the corneal samples by weighting them with the computed blending weights. The masks indicate which portions of the eye include the sclera part, which portions include the cornea part, and which portions include a transition region from sclera to cornea. In the transition region, the blending weights are used to blend the sclera mesh and the cornea mesh to show a smooth transition from the sclera to the cornea in the eyeball mesh. Therefore, cornea vertices from the cornea mesh are used in the eyeball mesh at the cornea regions, sclera vertices from the sclera mesh are used in the eyeball mesh for the sclera regions, and both sclera and cornea meshes are weighted and combined for areas in between.

Once the sclera and cornea representations are reconstructed for the sclera part and cornea part of the subject's eye, a representation of the iris part of the eye may be reconstructed. In contrast to the sclera, multi-view reconstruction may not be used to obtain the iris geometry because the refractive nature of the corneal surface distorts the views of the iris. Additionally, the cornea transitions smoothly in opacity from fully transparent to fully opaque at the sclera, and this smooth transition can confuse multi-view correspondence matching. For these reasons, a specific iris reconstruction technique is provided that is designed to handle these issues. Since the iris is coupled with the pupil, the technique begins by localizing the pupil in three dimensions. The iris geometry is then reconstructed and filtered, using the pupil as initialization. Finally, iris reconstructions from captures are combined with different pupil dilations, allowing the deformation of the iris to be parameterized and animated during pupillary response.

As noted, the iris reconstruction technique begins with pupil reconstruction. The pupil has a very prominent position at the center of the eye, which makes it visually important. Due to the prominent position of the pupil, artifacts on its boundary are clearly visible. Therefore, a reconstruction method is required for the pupil boundary that is robust with respect to perturbations like, for example, those caused by the flash highlight. The reconstructed pupil boundary is used to constrain the iris and also to guide the initial meshing of the iris.

The pupil is initialized by determining initial estimates using the pupil mask boundaries that were detected in image space using the classification results 604, 616, 620, and 624 described above. Using the mask boundaries corresponding to the pupil, an estimate of the pupil boundary location may be determined. Each pupil boundary from the different image masks is triangulated from multiple views, taking into account refraction at the cornea, and a circle is fit to the triangulated points. The required image correspondences for the triangulation are obtained from an optical flow calculation, which was already computed for the refraction constraints during the cornea optimization. For example, optical flow may be used to determine the correspondences of positions along the pupil boundary across the different images. For each point along the boundary in each image captured by each camera, a ray may be cast and refracted at the cornea. The various rays from the different images intersect at a given point, which gives a triangulated point on the pupil boundary. The process may be repeated for other points along the pupil boundary. An estimated 3D circle may then be fit to the various triangulated points to get an initial estimate of the pupil.

In some instances, the initial estimate may be inaccurate due to inconsistencies between pupil masks. In such instances, the technique refines the estimated 3D circle in an optimization that uses a number of data terms and a number of regularization terms. For example, two data terms and two regularization terms may be used. The data terms come from two additional cues about the pupil location, including (1) an image term $E_I$ that incorporates the result of an image-based pupil detection algorithm, and (2) a mesh term $E_M$ that incorporates an approximate 3D surface reconstruction of the pupil region, triangulated from image correspondences found using optical flow. The two regularization terms $E_C$ and $E_S$ control the overall shape and smoothness of the pupil. Based on these terms, an energy or error function is defined for the pupil as:

$$E = \lambda_I E_I + \lambda_M E_M + \lambda_C E_C + \lambda_S E_S, \quad (5)$$

which is minimized for a set of n pupil samples taken on the initial circle (e.g., 10 pupil samples, 20 pupil samples, 30 pupil samples, 40 pupil samples, 50 pupil samples, or any other appropriate number of pupil samples), with weights of $\lambda_I = 10$, $\lambda_M = 1000$, $\lambda_C = 10000$, and $\lambda_S = 1000$ for all data sets. The energy or error terms are described in more detail below.

With regard to the image term $E_I$, the initial pupil 3D circle is projected into the camera images and the images are blurred radially along the produced ellipses. A radial edge detector is then used to locate the edge between the pupil and the iris, and radial non-maximum suppression (NMS) is applied to the response. The image data term is defined as:

$$E_I = \frac{1}{n}\sum_{i=1}^{n}\|P(p_i) - p_i^{edge}\|^2, \quad (6)$$

where P(p) is the projection of sample point p into the image plane through the cornea, and $p^{edge}$ is the position of the closest point on the detected edge. The image term optimizes the projection of the 3D circle by minimizing distances between p and $p^{edge}$ so that the projection is close to the detected edges from the camera images in image space.

With regard to the mesh term $E_M$, an approximate 3D surface mesh in the vicinity of the pupil is created by triangulating rays from multiple views refracted at the corneal interface, again with the help of optical flow to provide correspondences, similar to that described above. The mesh term for the pupil location then includes the distances between the pupil samples and the generated mesh, and is given by:

$$E_M = \frac{1}{\sum_{i=1}^{n} c_i}\sum_{i=1}^{n} c_i\|p_i - p_i^{mesh}\|^2, \quad (7)$$

where the distances are weighted with the triangulation confidences c of the mesh. The triangulation confidence is defined as a linear function of the triangulation residuals, which maps a residual of 0 mm to a confidence of 1 and a residual of 0.05 mm to a confidence of 0 and clamps all the values outside this range.

The regularization terms include $E_C$ and $E_S$. The samples are allowed to deviate orthogonally from the perfect circle so as to allow more of an arbitrary shape. However, these deviations are penalized using the $E_C$ regularization term, which is defined as:

$$E_C = \frac{1}{n}\sum_{i=1}^{n}\|p_i - p_i^{circle}\|^2 \quad (8)$$

where $p^{circle}$ is the corresponding point of p on the circle. The Ec term ensures a pupil shape that is close to a perfect circle.

To obtain a smooth pupil where variations between the circle samples is minimal, strong changes in the deviations from one sample to the next is also penalized using the $E_S$ regularization term, which is defined using the following smoothness term:

$$E_S = \frac{1}{n}\sum_{i=1}^{n}[(2r_i - r_i + 1 - r_i - 1)^2 + (2\sigma_i - o_i + 1 - o_i - 1)^2], \quad (9)$$

where r is the radial and o is the orthogonal component of the offset with respect to the circle.

Figure 15A:
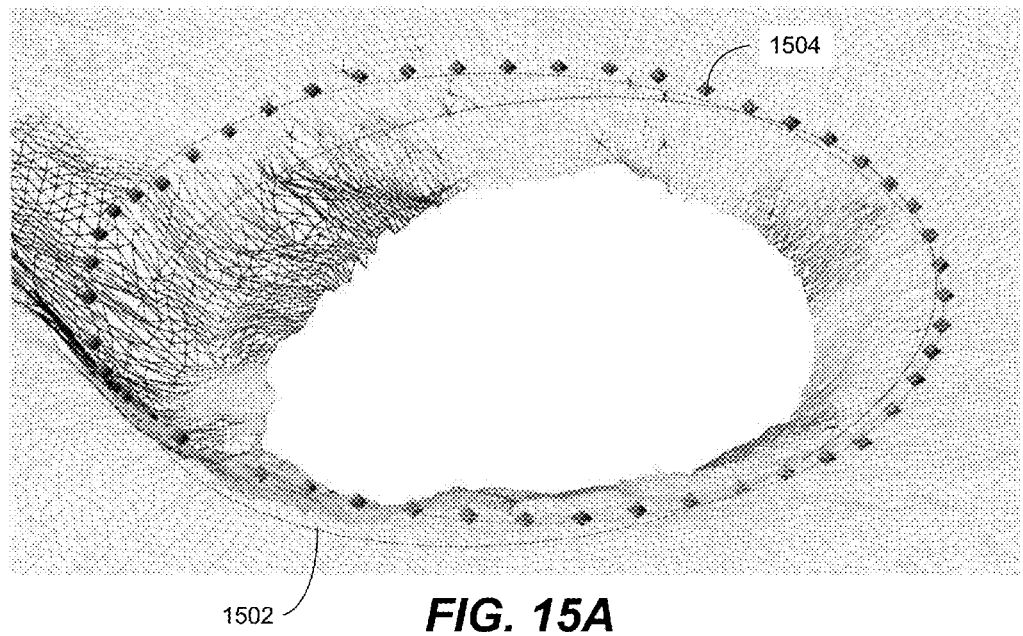
FIG. 15A illustrates an example of pupil boundary samples, in accordance with one embodiment of the present invention.
Figure 15B:
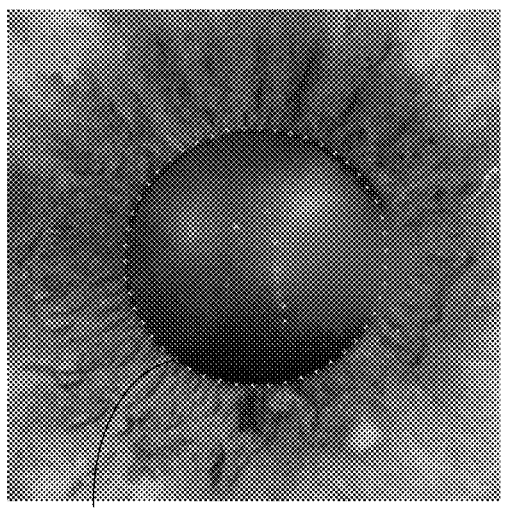
FIG. 15B illustrates an example of pupil boundary samples projected onto an image, in accordance with one embodiment of the present invention.
Figure 15C:
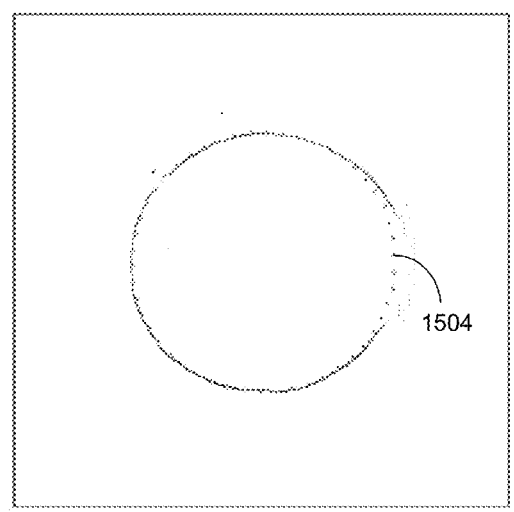
FIG. 15C illustrates an example of pupil boundary samples overlaid onto the response of a pupil edge detector, in accordance with one embodiment of the present invention.

The sum of all these terms is minimized (e.g., using the Levenberg-Marquardt algorithm, a Gauss-Newton algorithm, a steepest descent algorithm, a conjugate gradient algorithm, or any other known nonlinear optimization) to find the position, the radius, and the per-sample deviations from a circle of the pupil. During the optimization, the normal of the pupil circle is constrained to the normal of the plane fit to iris mesh samples taken a certain distance away (e.g., 1 mm, 2 mm, or other appropriate distance) from the initial pupil boundary estimate to be more robust. FIG. 15A illustrates the resulting sample positions in 3D. Given an initial pupil boundary estimate 1502 from the triangulated image-based pupil masks, the reconstruction technique solves for the optimal pupil boundary sample positions 1504. FIG. 15B illustrates the resulting sample positions 1504 projected onto an image. FIG. 15C illustrates the resulting sample positions overlaid onto the response of the pupil edge detector.

Once the pupil boundary is reconstructed, the iris mesh is generated. In a first step, the reconstructed pupil boundary is used to initialize the iris mesh to determine the topology of the iris. Starting with a closed uniform B-Spline that is fit to the optimized pupil samples, the spline is scaled radially in 0.025 mm (or other appropriate distance) steps to create a sequence of larger and larger rings up to an iris radius of 7 mm (or other appropriate radius). These rings are sampled a certain number of times (e.g., 100, 200, 300, 400, 500, 600, or other appropriate number of times) and a triangle mesh is created. The triangle mesh will serve as the topology for the iris.

In a second step, the correct position of each iris vertex is reconstructed to determine the position of the iris mesh. Each vertex is projected (through the cornea) into a reference camera, where flow-based correspondences to other views are computed (e.g., using optical flow). The vertex position is triangulated by minimizing the squared distances between the vertex and the refracted rays formed by the correspondences. This minimization is equivalent to minimizing the surface error, as described above with respect to equations (1)-(4). In addition, the rays are weighted by the root mean square difference of the corresponding 7×7 pixel blocks in image space. In order to reduce high frequency noise, the entire mesh reconstruction process is repeated for a second reference camera to obtain a second mesh hypothesis which is combined with the first one through weighted averaging.

The reconstructed iris mesh may be noisy and distorted at the boundaries due to the translucent sclera affecting the optical flow. Various operations may be performed to filter the iris mesh. For example, spike filtering may be performed. Spikes are detected by computing a 3-ring neighborhood around each vertex. If the distance between the vertex and the mean of the neighboring vertices exceeds a threshold (e.g., set to 0.05 mm), then the vertices inside the ring are smoothed by solving a Laplacian system, keeping the rest of the vertices fixed. Boundary deformation may also be performed. For example, two criteria are used to label distorted boundary vertices: a threshold on the triangulation residuals (set to 0.05 mm) and an angle threshold between the smoothed vertex normal and the normal of the pupil set to 30 degrees. The labeled region may be dilated and those vertices may be smoothed in the normal direction. Mesh relaxation may also be performed. The mesh is relaxed locally to improve the triangulation by removing skinny or overlapping triangles. Finally, the vertices at the pupil boundary may be constrained to the detected pupil shape. The constraint is enforced with a local Laplacian system, where the pupil vertices as well as all mesh vertices farther than 1 mm from the pupil are constrained. The vertices in-between are deformed but the local shape is preserved. Finally, the two independently triangulated and cleaned mesh hypotheses are averaged to create the iris mesh.

Mesh propagation may then be performed. Iris reconstructions from captures are combined with different pupil dilations. Each mesh is reconstructed independently, with different topology and vertex counts. A new set of iris meshes are computed that are in vertex-correspondence, allowing a per vertex deformation model to be computed. The mesh propagation begins by computing per camera optical flow between neighboring poses. Since the vertices are propagated from one pose to the next, drift might accumulate. To minimize the total amount of drift, a reference pose in the middle of the dilation sequence is selected and the optical flow is computed in both dilation directions from there. To find the vertex correspondences, each vertex is projected from the source mesh into all the target pose cameras, taking into account the refraction at the cornea. With the resulting image positions and the optical flows, a set of rays are computed that are refracted at the cornea and intersected with the iris of the target pose. The target pose vertex is computed as the median of all the intersections. To ensure a clean pupil, the pupil constraint is enforced and the mesh is relaxed in the same way as described above.

Temporal smoothing and interpolation is then performed. In order to animate the pupil dilation, the captured pupil poses are used as keyframes and interpolation is performed linearly in-between. In practice, the dilation of the pupil may not be accurately controlled, and so the pupil diameter may tend to decrease in irregular steps. This can lead to multiple poses with very similar diameters and geometry, but with different high frequency reconstruction noise, which leads to artifacts when interpolating. In order to smoothly integrate meshes from similar pupil radii, two linear regression models are computed for all poses within a certain distance (e.g., 1 mm) pupil radius. The first regression model expresses the vertex position and the second model the Laplacian vector as a function of the pupil radius. The smoothed mesh is solved for by evaluating both models and solving the resulting Laplacian system with equal weights given to the Laplacians and the positions.

Iris textures can be computed from a single view, but these textures may contain undesired artifacts like highlights, washed out regions close to the boundary, dust on the cornea, or the like. These artifacts can be attenuated by combining the textures from multiple views of the same iris dilation. A contribution map is computed for each view which is set to 1 if the pixel is the most saturated from all the candidates and to 0 otherwise. These maps are then blurred with a small Gaussian kernel of 3 pixels. Based on these contribution maps, the textures from the different views are blended into a single texture. Picking the most saturated pixels will reduce artifacts caused by illumination pollution from the flash light and by superposition of the white sclera at the semi-transparent sclera-cornea transition alike. Then, the textures from several iris dilations are combined using the median to attenuate shading changes caused by the deforming iris.

Using the above-described techniques, all the visible parts of the eye may be accurately reconstructed, including the sclera, the transparent refractive cornea, and the non-rigidly deforming colored iris. Other objects may also include a surface that is located behind a refractive surface. For example, glass, water, a cornea part of an eye, as well as many other objects, include refractive surfaces. Using water as an example, an object submerged under water may be distorted due to the refractive nature of the water. Another example may include an object with an opaque surface that is cast inside or behind glass, such as an object in a snow globe, an object under a magnifying glass or other lens, or the like. Yet another example may include an object with an opaque surface that is cast in amber or other material. Similar techniques as those described above may be used to reconstruct the geometry of the surface behind the refractive surface, and also to reconstruct the geometry of the refractive surface.

Figure 16:
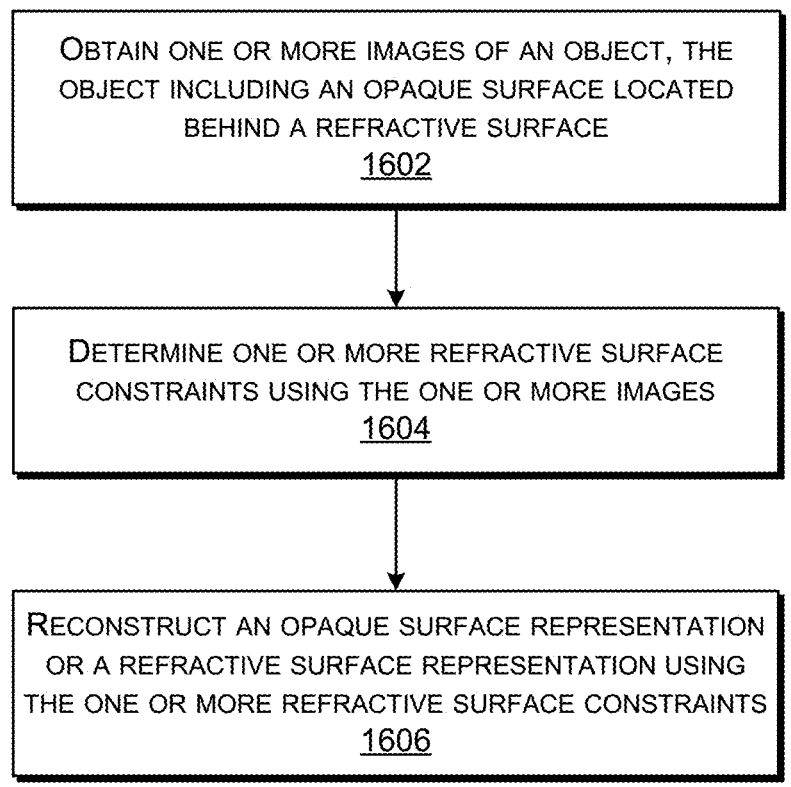
FIG. 16 illustrates an example of a process of reconstructing one or more surfaces of an object, in accordance with one embodiment of the present invention.

FIG. 16 illustrates an example of a process 1600 of reconstructing one or more surfaces of an object including an opaque surface. Process 1600 is illustrated as a logical flow diagram, the operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be combined in any order and/or in parallel to implement the processes.

Additionally, the process 1600 may be performed under the control of one or more computer systems configured with executable instructions and may be implemented as code (e.g., executable instructions, one or more computer programs, or one or more applications) executing collectively on one or more processors, by hardware, or combinations thereof. The code may be stored on a computer-readable storage medium, for example, in the form of a computer program comprising a plurality of instructions executable by one or more processors. The computer-readable storage medium may be non-transitory.

Figure 32:
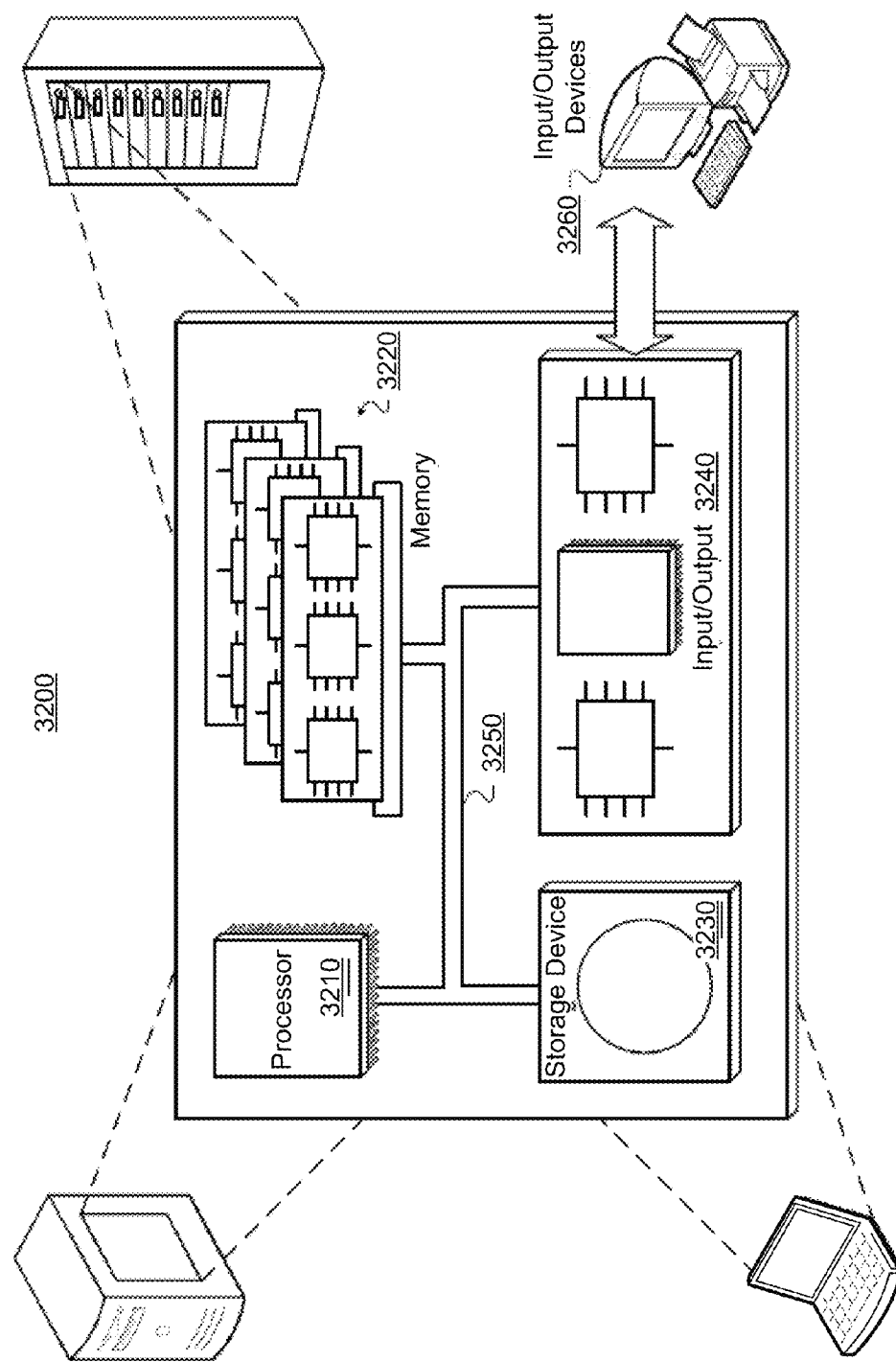
FIG. 32 shows an example of a computer system that may be used in various embodiments of the present invention.

In some aspects, the process 1600 may be performed by a computing device, such as the computer system 3200 shown in FIG. 32.

At 1602, the process 1600 includes obtaining one or more images of an object. The object includes an opaque surface that is located behind a refractive surface. The images may be obtained using a system similar to that illustrated in FIGS. 4A-4B. In some embodiments, the surface of the object is not opaque, and may instead be transparent or translucent. In some embodiments, the object includes an eye, the refractive surface includes a cornea part of the eye, and the opaque surface includes an iris part of the eye. In some embodiments, the object includes an object that is submerged under water, and the refractive surface includes a surface of the water. In some embodiments, the object includes an object that is cast under a layer of material, and the refractive surface includes a surface of the material. The material may include glass, amber, water, or any other material that includes a refractive surface. In any case, the opaque surface is distorted due to the refractive nature of the refractive surface.

At 1604, the process 1600 includes determining one or more refractive surface constraints using the one or more images. The one or more refractive surface constraints constrain one or more characteristics of the refractive surface. For example, the one or more characteristics of the refractive surface may include a position or a surface normal of the refractive surface. In some examples, the one or more refractive surface constraints may include one or more reflection constraints, one or more refraction constraints, and/or one or more position constraints. In some examples, the one or more reflection constraints are obtained by shining one or more lights onto the refractive surface. For example, one or more light-emitting diodes (e.g., color lights (4) in FIG. 4B) may be used to produce highlights reflecting off of the refractive surface. In some examples, the one or more position constraints are provided by a user that knows the surface positions of the refractive surface. In some examples, the position constraints may be drawn or painted by a user. In some examples, the position constraints may be reconstructed from scans or stereo reconstructions of the refractive surface.

At 1606, the process 1600 includes reconstructing an opaque surface representation or a refractive surface representation using the one or more refractive surface constraints. The opaque surface representation represents the opaque surface of the object and the refractive surface representation representing the refractive surface of the object. Reconstructing the opaque surface representation includes undoing distortion introduced by the refractive surface. For example, the distortion may be undone by tracing rays through the refractive surface and refracting them, as described above. For example, a stereo-type reconstruction may be performed with a possible additional bend in the ray. Reconstructing the refractive surface representation includes employing an optimization method using the one or more surface constraints. Any of the techniques described above with respect to equations (1)-(4) may be used to reconstruct the refractive surface. For example, a non-linear optimization, as described above, may be used to reconstruct the refractive surface representation.

In embodiments in which the object is an eye, the process 600 may include reconstructing a sclera representation using the one or more images, the sclera representation representing a sclera part of the eye. Reconstructing the sclera representation may include segmenting the one or more images of the eye to identify the sclera part, the cornea part, and the iris part of the eye in the one or more images, generating one or more mesh representations of the sclera part, wherein a mesh representation of the sclera part is generated by projecting a segmented image of the eye onto a mesh representation of the eye, aligning poses in the one or more mesh representations of the sclera part to a reference pose, and merging the one or more mesh representations of the sclera into a merged sclera mesh.

Figure 17:
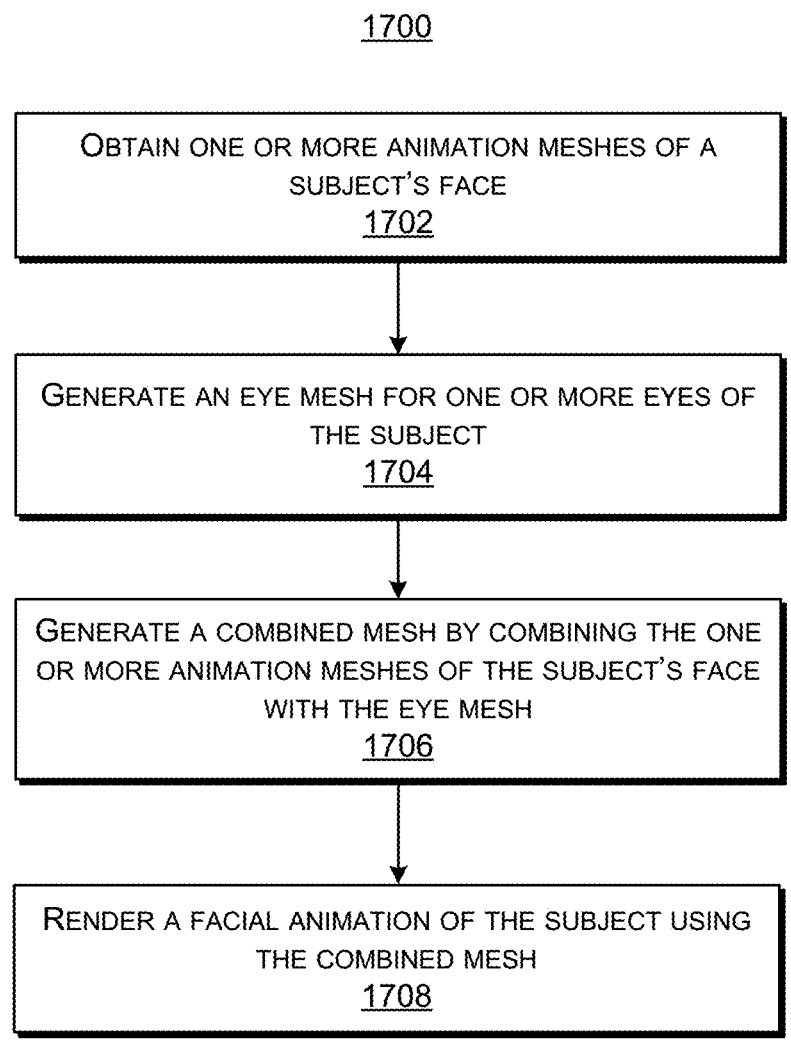
FIG. 17 illustrates an example of a process of rendering a facial animation of a subject's face including reconstructed eyes of the subject, in accordance with one embodiment of the present invention.

As noted in the description of FIG. 16, the object may include a subject's eye. The subject's eye may be reconstructed, and used to animate the subject's face including the eye. FIG. 17 illustrates an example of a process 1700 of rendering a facial animation of the subject. Process 1700 is illustrated as a logical flow diagram, the operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be combined in any order and/or in parallel to implement the processes.

Additionally, the process 1700 may be performed under the control of one or more computer systems configured with executable instructions and may be implemented as code (e.g., executable instructions, one or more computer programs, or one or more applications) executing collectively on one or more processors, by hardware, or combinations thereof. The code may be stored on a computer-readable storage medium, for example, in the form of a computer program comprising a plurality of instructions executable by one or more processors. The computer-readable storage medium may be non-transitory.

In some aspects, the process 1700 may be performed by a computing device, such as the computer system 3200 shown in FIG. 32.

At 1702, the process 1700 includes obtaining one or more animation meshes of a subject's face. For example, to produce an animated character representing the subject, an animation mesh generator may generate an animation mesh that represents the three-dimensional shape of the subject's face and that can be used for animation. An animation mesh may be produced from one or more types of information, such as one or more captured camera images. User input may also be used to produce an animation mesh. For example, the animation mesh may be produced by an artist without the use of an animation mesh generator, or in combination with an animation mesh generator. Graphical software packages may also be used by the artist or in conjuncture with the animation mesh generator to generate the animation mesh. In some examples, an artist may generate an animation mesh from one or more of captured images by applying a high resolution grid. An animation mesh may include a grid that conforms to the shape of the subject's face. The animation mesh may include vertices that represent features of the subject's face.

At 1704, the process 1700 includes generating an eye mesh for one or more eyes of the subject. Details relating to step 1704 for generating the eye mesh are described below with respect to FIG. 18. In some embodiments, the eye mesh is separate from the one or more animation meshes of the subject's face. The eye mesh may be generated using different images than the images used to generate the one or more animation meshes. In some embodiments, a separate eye mesh may be generated for each of the subject's eyes.

At 1706, the process 1700 includes generating a combined mesh by combining the one or more animation meshes of the subject's face with the eye mesh. In some embodiments, a deformation method may be used, such as Laplacian deformation, to combine the eye mesh and the one or more animation meshes.

Figure 30:
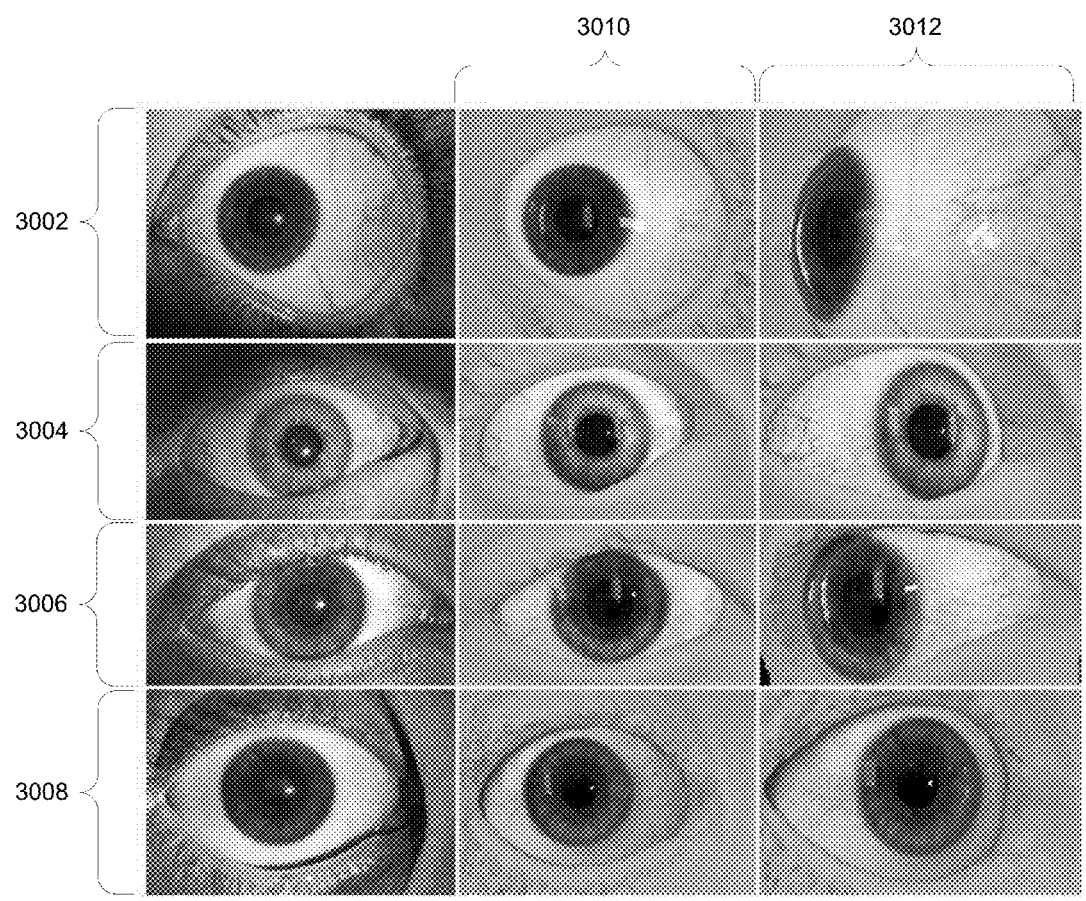
FIG. 30 illustrates an example of different views of results obtained by combining a reconstructed eye using the techniques described herein with partial face scans, in accordance with one embodiment of the present invention.
Figure 31:
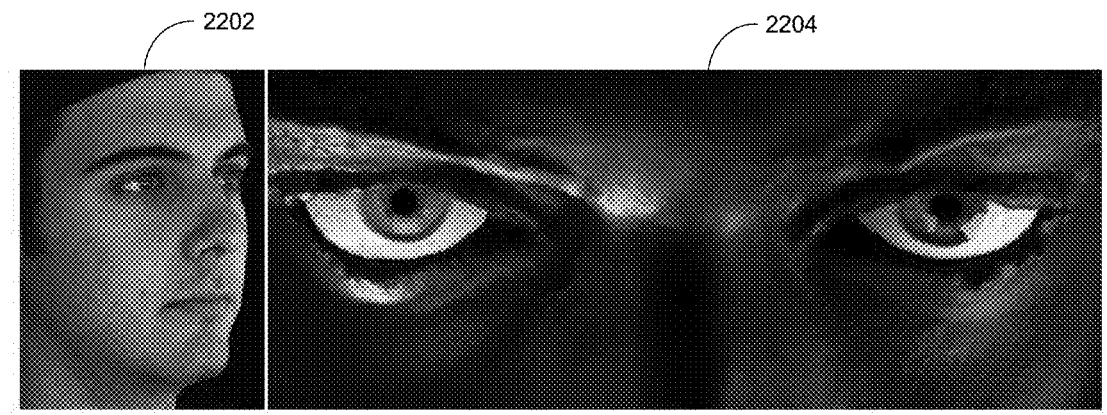
FIG. 31 illustrates an example of results obtained by combining both reconstructed eyes of a subject using the techniques described herein with a face scan of the subject, in accordance with one embodiment of the present invention.

At 1708, the process 1700 includes rendering a facial animation of the subject using the combined mesh. Any appropriate techniques for rending facial animations using a mesh can be used to render the facial animation. Examples of rendered facial animations of subjects are shown in FIGS. 30 and 31, and are discussed further below. The rendered facial animation may be animated using motion information. Any appropriate techniques for animating graphical characters can be used to animate the facial animation.

Figure 18:
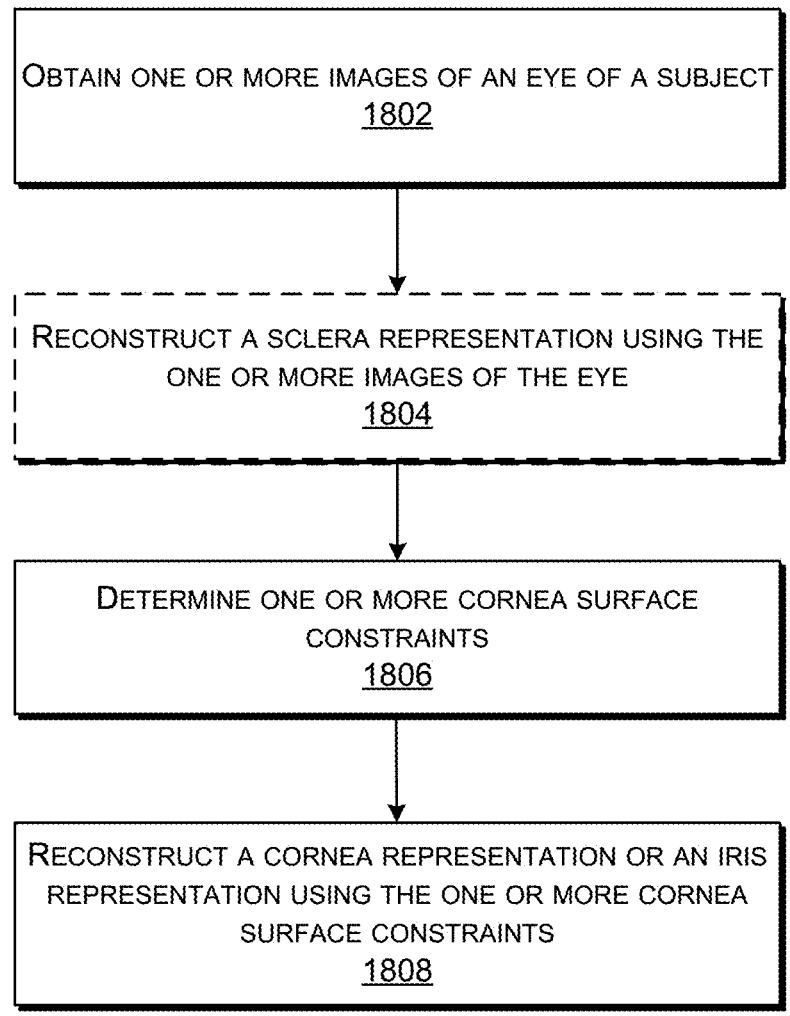
FIG. 18 illustrates an example of a process of reconstructing parts of an eye of a subject, in accordance with one embodiment of the present invention.

FIG. 18 illustrates an example of a process 1704 of generating the eye mesh. The process 1704 includes reconstructing parts of an eye of a subject. Process 1704 is illustrated as a logical flow diagram, the operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be combined in any order and/or in parallel to implement the processes.

Additionally, the process 1704 may be performed under the control of one or more computer systems configured with executable instructions and may be implemented as code (e.g., executable instructions, one or more computer programs, or one or more applications) executing collectively on one or more processors, by hardware, or combinations thereof. The code may be stored on a computer-readable storage medium, for example, in the form of a computer program comprising a plurality of instructions executable by one or more processors. The computer-readable storage medium may be non-transitory.

In some aspects, the process 1704 may be performed by a computing device, such as the computer system 3200 shown in FIG. 32.

At 1802, the process 1704 includes obtaining one or more images of an eye of a subject. The one or more images may be obtained using the system 400 illustrated in FIGS. 4A-4B. The one or more images may be captured using multiple cameras, or a single camera.

Process 1704 includes optional step 1804 (as indicated by the dotted outline of the box for step 1804), including reconstructing a sclera representation using the one or more images of the eye. The sclera representation represents a sclera part of the eye. In some embodiments, the process 1704 does not include reconstructing the sclera representation, and may include only reconstructing a cornea representation and/or a iris representation (step 1808 below). In some embodiments, reconstructing the sclera representation using the one or more images of the eye includes segmenting the one or more images of the eye to identify the sclera part, the cornea part, and the iris part of the eye in the one or more images, and generating one or more mesh representations of the sclera part. A mesh representation of the sclera part is generated by projecting a segmented image of the eye onto a mesh representation of the eye. Reconstructing the sclera representation further includes aligning poses in the one or more mesh representations of the sclera part to a reference pose, and merging the one or more mesh representations of the sclera into a merged sclera mesh. Further details of the technique for reconstructing the sclera representation are discussed above with respect to FIGS. 3-8.

At 1806, the process 1704 includes determining one or more cornea surface constraints. The one or more cornea surface constraints include one or more reflection constraints, one or more refraction constraints, and one or more position constraints. As described above, the one or more reflection constraints are obtained by shining one or more lights onto the cornea part of the eye. For example, one or more light-emitting diodes (e.g., color lights (4) in FIG. 4B) may be used to produce highlights reflecting off of the refractive cornea surface. As further described above, the one or more position constraints are obtained from a merged sclera mesh. Further details of the cornea surface constraints are discussed above with respect to FIGS. 9A-15C.

At 1808, the process 1704 includes reconstructing a cornea representation or an iris representation using the one or more cornea surface constraints. In some embodiments both the cornea representation and the iris representation can be reconstructed at step 1808. The cornea representation represents a cornea part of the eye, and the iris representation represents an iris part of the eye. As described above, reconstructing the cornea representation includes employing an optimization method using the one or more cornea surface constraints. For example, a non-linear optimization may be used. As further described above, reconstructing the iris representation includes detecting a boundary of a pupil part of the eye using a segmented image of the eye and refining the boundary of the pupil by generating a ray from a point on the boundary of the pupil part, refracting the ray using a refraction index, and intersecting corresponding rays from the point in multiple images of the pupil from multiple camera views. Reconstructing the iris representation further includes determining a topology of a mesh representation of the iris part using the refined boundary of the pupil. Further details relating to the cornea and iris reconstructions are discussed above with respect to FIGS. 3 and 9A-15C.

Using the above-described techniques, one or more surfaces of an object that includes an unknown surface located behind a refractive surface may be reconstructed. For example, all the visible parts of the eye may be accurately reconstructed, including the sclera, the transparent refractive cornea, and the colored iris that is located behind the refractive cornea, thus providing compelling results for generating realistic reconstructions of the eye. FIGS. 19-31 illustrate various quantitative and qualitative results of the reconstruction systems and techniques described herein, specifically with respect to the parts of an eye. Results of the eye capture techniques are shown by illustrating the reconstructions of a variety of human eyes, each with its own intricacies and details.

Figure 19:
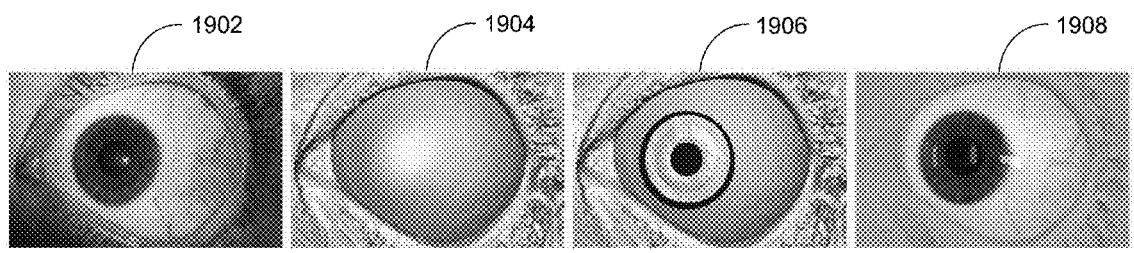
FIG. 19 illustrates an example of an input image, a reconstructed eyeball depicted in the image, a reconstructed iris geometry depicted in the image, and a final render of a representation of the eyeball, in accordance with one embodiment of the present invention.

FIG. 19 illustrates an input image 1902, a reconstructed eyeball geometry 1904 of the eyeball in the input image 1902, an iris geometry 1906 of the iris of the eyeball in the input image, and a final render 1908 using the reconstructed eyeball and iris. The final render 1908 is from a novel viewpoint under different illumination.

Figure 20A:
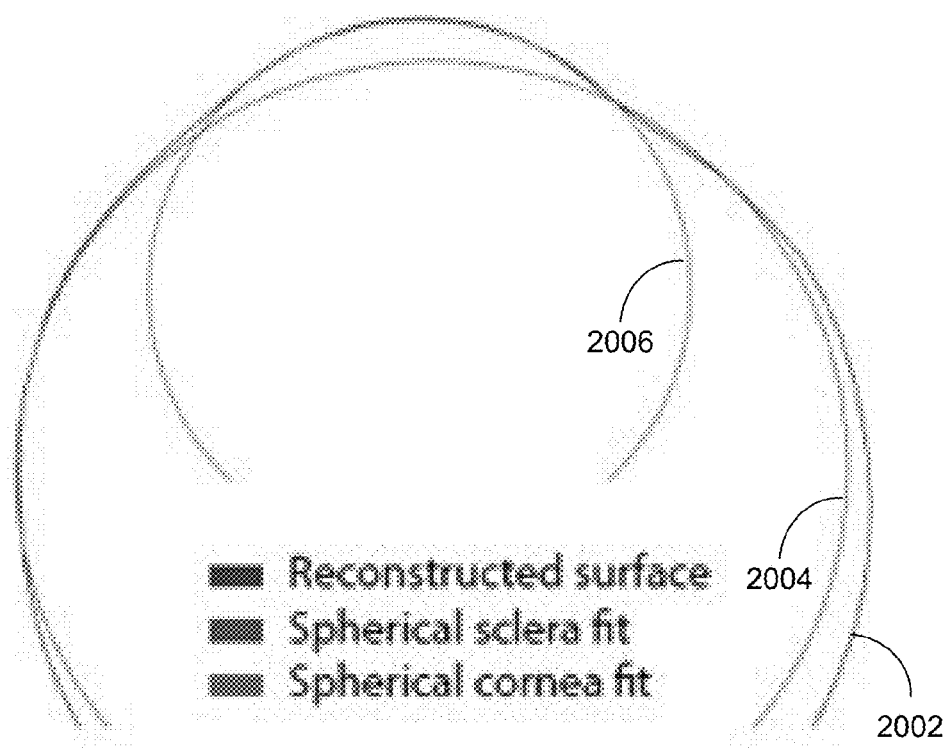
FIG. 20A illustrates an example of comparisons between performance results obtained using the reconstruction techniques described herein and performance results obtained using a sphere approximation technique.
Figure 20B:
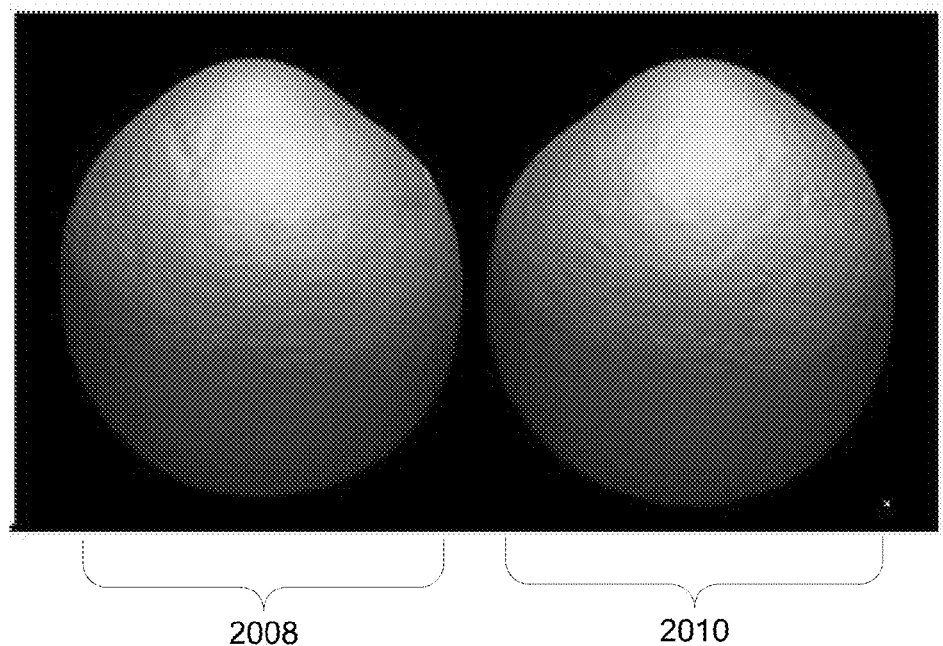
FIG. 20B illustrates an example of reconstructed left and right eyes of a subject using the reconstruction techniques described herein, in accordance with one embodiment of the present invention.

As illustrated in FIG. 20A, the results can be shown first by analyzing the common assumption that eyes can be modeled as two spheres, a large sphere 2004 for the eyeball and a smaller sphere 2006 for the cornea. This assumption is inaccurate, as illustrated in FIG. 20A, by overlaying a cross-section 2002 of a captured eye, reconstructed using the techniques herein, on top of the two-sphere model with spheres 2004 and 2006. Furthermore, it is often assumed that an eye is symmetric about the view vector and that the left and right eye can be modeled similarly. As illustrated in FIG. 20B, by reconstructing both the left eye 2008 and right eye 2010 of a subject, it can be demonstrated that each eye is in fact unique and shows strong asymmetry individually, but when combined the expected left/right symmetry is clearly visible. The results of the techniques described herein have the potential to change how eyes are traditionally modeled in computer graphics.

Figure 21:
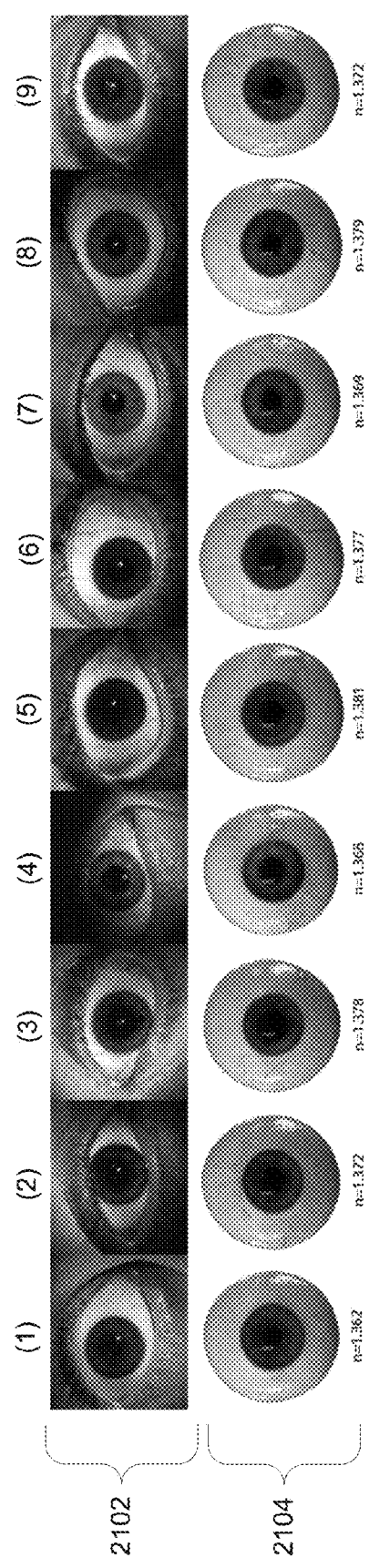
FIG. 21 illustrates an example of a dataset comprising different iris colors, individual sclera textures, and a unique geometry for each eye, along with an index of refraction for each eye.

The eye-capture techniques described herein are robust. The robustness of the techniques can be highlighted by reconstructing nine different eyes from six different subjects, as shown in FIG. 21. A full set of reconstructions 2104 is shown for different eyes 2102 that are numbered (1)-(9) in FIG. 21. The full set of reconstructions 2104 contains a variety of different iris colors, surface details (such as sclera textures and shapes), textures, and overall eye geometries or shapes. Each eye has unique details, but the differences between people are more significant than the differences between the two eyes of the same person, which helps to validate the reconstruction results. For example, the two brown eyes (5) and (6) are larger than the rest. The eyes (5) and (6) represent the eyes of a subject with severe myopia, or short-sightedness, which is often correlated with larger-than normal eyes. The measured index of refraction n is listed under each eye.

Figure 22A:
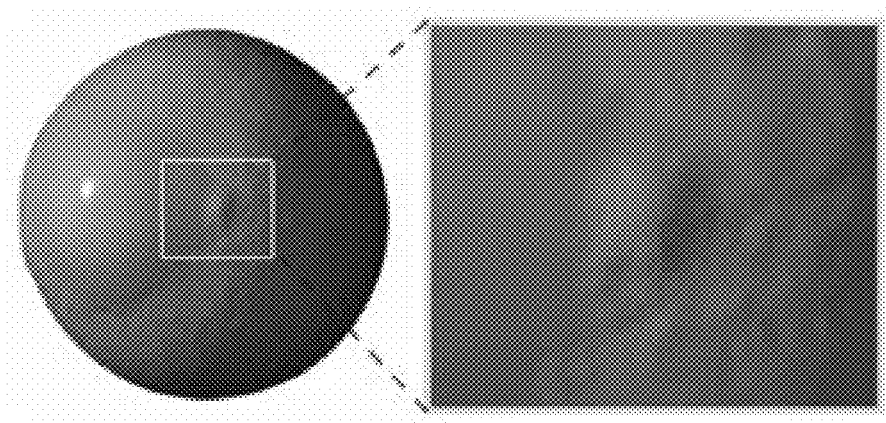
FIG. 22A illustrates an example of a finescale detail of a subject's eye reconstructed using the reconstruction techniques described herein.
Figure 22B:
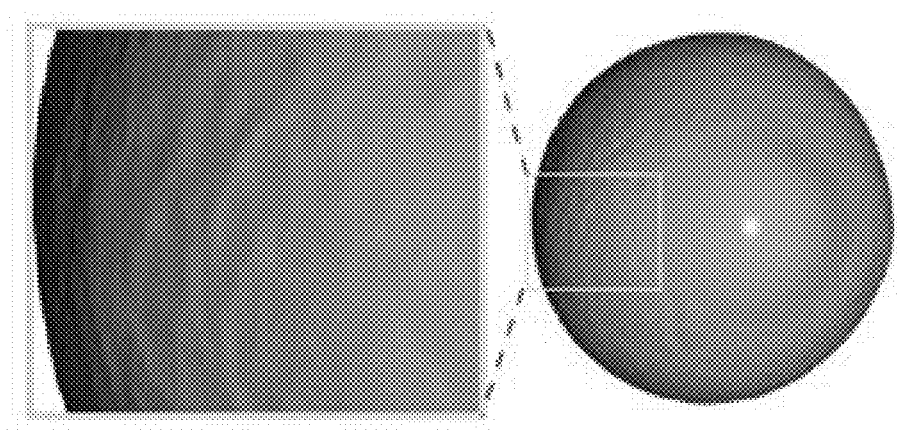
FIG. 22B illustrates an example of finescale surface variation of a subject's eye reconstructed using the reconstruction techniques described herein.

Every human eye is unique and contains minor intricacies that add to the identity of the person. The reconstruction capture techniques described herein aim to reconstruct all the visible intricacies of the eye. For example, the sclera reconstruction described above is able to acquire high-resolution surface variation including various small details specific to the subject. For example, FIG. 22A illustrates a reconstructed eye with a Pingueculas, which includes a degeneration of the fibers of the sclera that results in a small bump on a subject's eye. FIG. 22B illustrates detailed surface variation that is unique to the eye.

Figure 23:
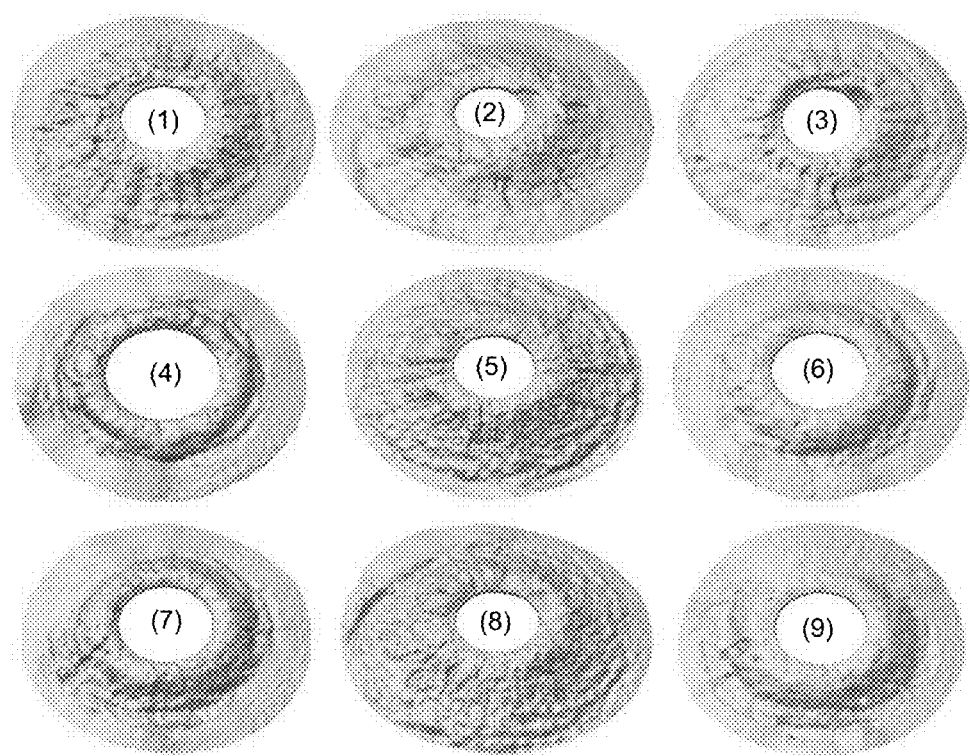
FIG. 23 illustrates an example of differences in detail of various captured irises of different subjects.
Figure 24:
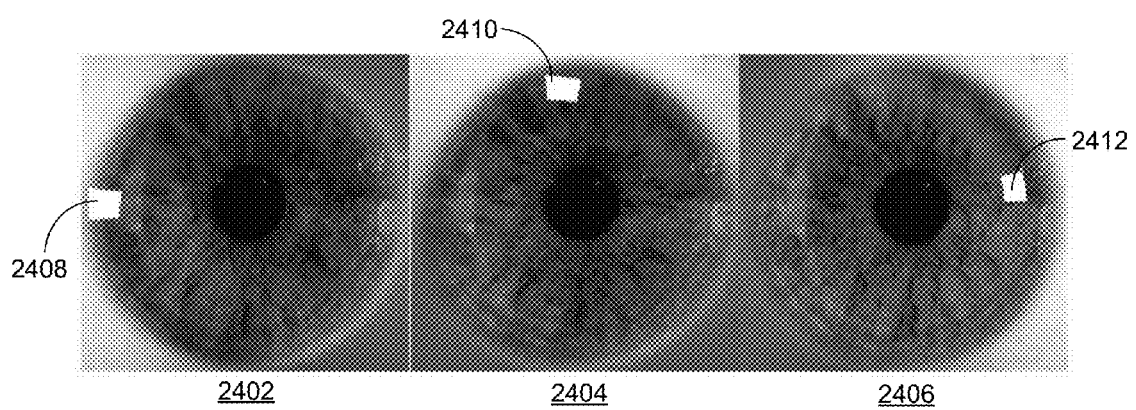
FIG. 24 illustrates an example of detailed geometry and texture of an iris rendered in high-quality with refraction through the cornea and three different light positions.
Figure 25A:
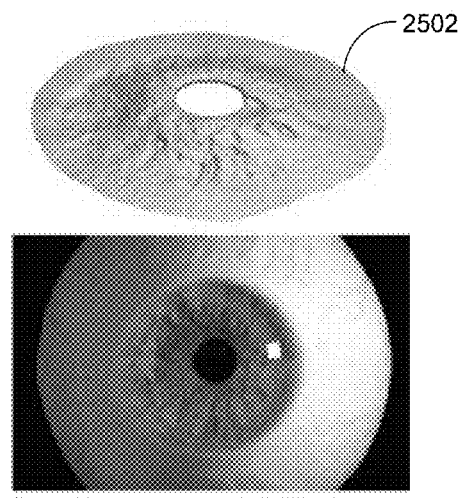
FIG. 25A illustrates an example of an iris of a subject measured at a first amount of pupil dilation.
Figure 25B:
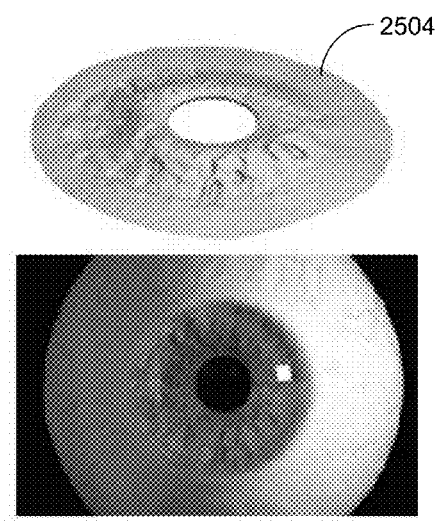
FIG. 25B illustrates an example of an iris of a subject measured at a second amount of pupil dilation.
Figure 25C:
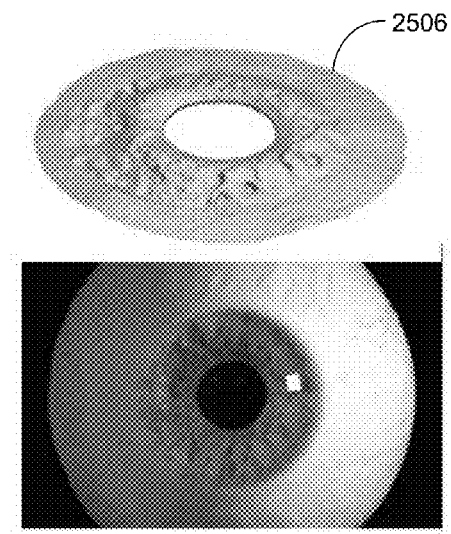
FIG. 25C illustrates an example of an iris of a subject measured at a third amount of pupil dilation.
Figure 26:
FIG. 26 illustrates an example of iris deformations during various pupil dilations for two different irises.

The iris also includes unique features for different subjects. FIG. 23 illustrates one pose of reconstructed irises for the nine actors, visualized on their own with shading for comparing the geometry. As illustrated, the individuality of iris shape from eye to eye is clearly visible, again highlighting the importance of capturing real eyes using the techniques described herein. FIG. 24 shows close-up views 2402, 2404, and 2406 of a captured iris with both surface details and texture, rendered with refraction through the cornea and three different light positions 2408, 2410, and 2412.

One interesting feature of human eyes is the time-varying deformation of the iris during pupillary response. The techniques described herein are able to recover this deformation, as illustrated for one actor in FIGS. 25A-25C. The pupil is dilated at various amounts. As the pupil changes size, the reconstructions 2502, 2504, and 2506 show that the iris dilator muscle creates significant out-of-plane deformation as the pupil becomes larger, which largely contributes to the realistic appearance of the eye. To further illustrate how unique this effect is for each iris, deformations of the irises 2402 and 2404 are shown from a side view in FIG. 26 for two additional irises 2402 and 2404, and three pupil radii, including open 2406, halfway 2408, and closed 2410.

Figure 27:
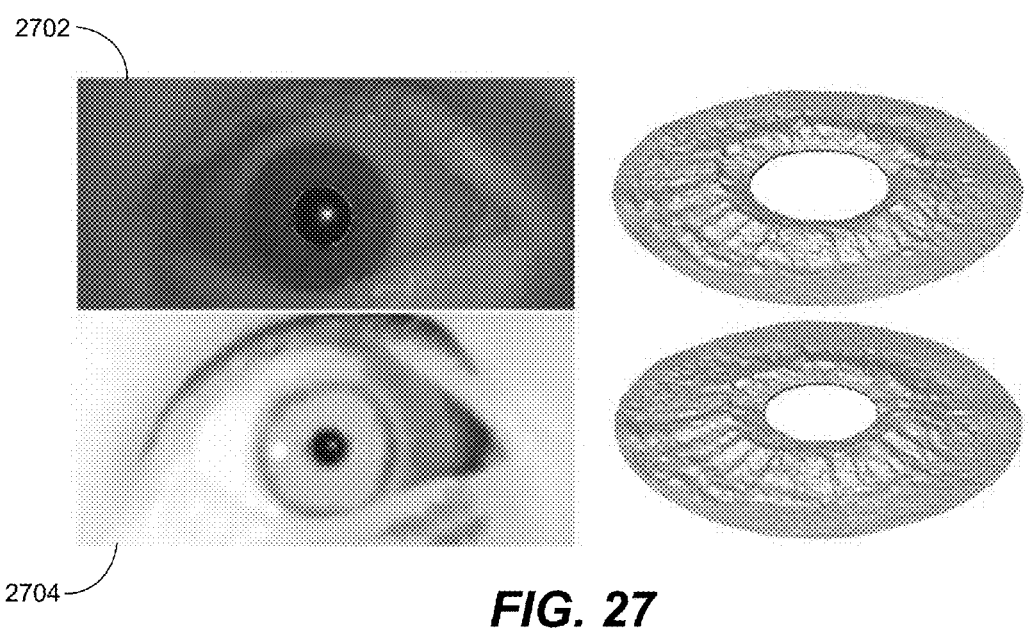
FIG. 27 illustrates a first example of an application for iris animation, in accordance with one embodiment of the present invention.
Figure 28:
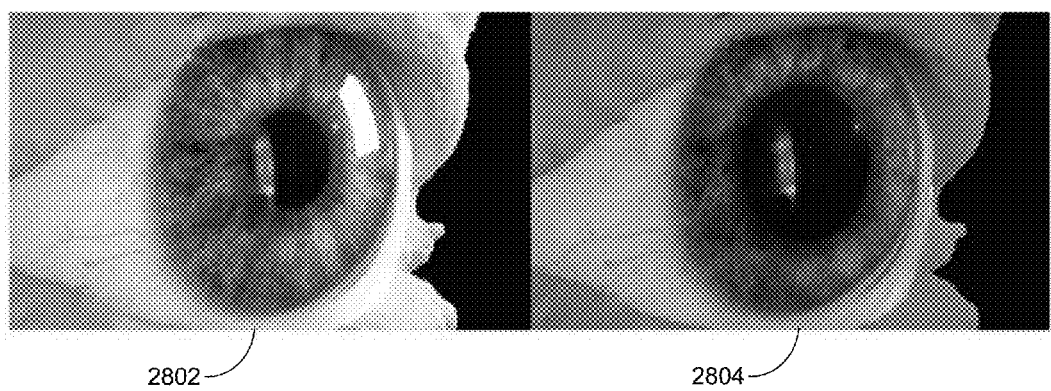
FIG. 28 illustrates a second example of an application for iris animation, in accordance with one embodiment of the present invention.

The ability to reconstruct a per-vertex deformation model for the iris during pupil dilation allows animation of the captured eyes of the subject. For example, the measured iris deformation can be applied in a pupil dilation animation. Two different applications for iris animation are shown in FIGS. 27 and 28. The application shown in FIG. 27 includes a motion capture scenario. Analogous to the way facial animation rigs may be built from high-quality scan data and then later animated from low-resolution mo-cap markers, the captured irises can be animated from a single low-quality video stream. For example, the pupil size of a subject can be captured in each frame of such a video, such as frames 2702 and 2704, and the corresponding iris shape can be computed for a captured subject. In FIG. 27, the subject's pupil is tracked in a single infra-red video and the corresponding radius is applied to the eye model.

A second application for iris animation shown in FIG. 28 may include automatically making a digital character of the subject respond to lighting changes in a 3D environment. Using predicted pupillary response curves, the captured iris geometry can be animated to show a character dynamically responding to a light source turning on in frame 2802 and responding to a light turning off in frame 2804.

Figure 29:
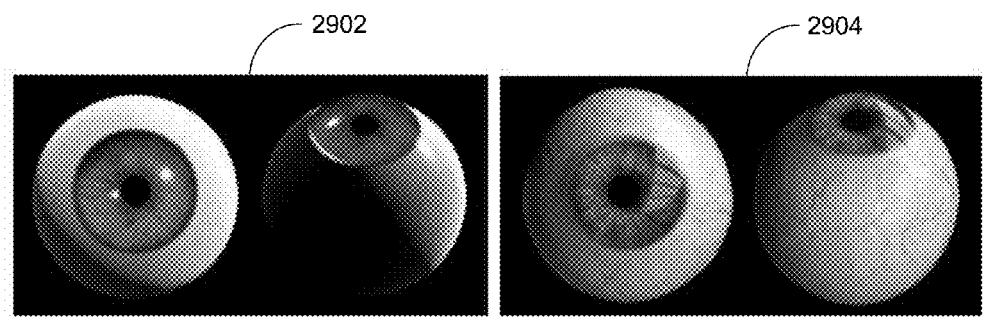
FIG. 29 illustrates an example of a comparison between results obtained using the reconstruction techniques described herein and results obtained using another technique.

FIG. 29 includes a comparison of the results of the techniques described herein with other techniques. The frame 2902 illustrates a reconstructed eye generated using traditional techniques, which employs a generic eyeball model combined with a heuristic to synthesize the iris morphology. The frame 2904 illustrates a reconstructed eye generated using the reconstruction techniques described herein. As can be seen by the intricacies of the reconstructed eye shown in frame 2904, the techniques described herein excel in quality versus traditional techniques, and more faithfully capture the uniqueness and realism of eyes. In particular, the reconstructions techniques described herein show the asymmetric shape of the sclera and fine scale surface variation. The iris geometry is reconstructed rather than heuristically synthesized, and even small defects are recovered, such as a Pingueculas and the non-circular transition between sclera and iris.

In order to provide context for visualizing the captured eyes, the eyes can be combined with partially reconstructed face scans of the subjects. In some examples, a combination process may be used that automatically fits the face geometry of a subject around the back of the eyeball using, for example, a Laplacian deformation scheme. The result is sufficient to simulate an eye socket for holding the reconstructed eye. Several eye reconstruction results for different subjects 3002, 3004, 3006, and 3008 are shown in FIG. 30. The eye reconstruction results are rendered from multiple viewpoints 3010 and 3012 that include different environmental lighting. Using such techniques to combine face scans with eyes allows the reconstruction results to be used in the visual effects industry for creating digital doubles.

Using the reconstruction techniques described herein to capture real eyes can have a large impact in creating artistic digital doubles, which is often performed for visual effects in films. As shown in FIG. 31, both captured eyes of a subject 2202 can be combined together with a face scan of the subject to create a compelling rendition 2204 of an artistically designed digital human character. Such a result would traditionally take significant artistic skill and man-hours to generate, in particular if the digital character should closely resemble a real subject. However, the techniques described herein can create the result shown in frame 2204 using less time than traditional methods.

Referring to FIG. 32, a schematic diagram is shown of an example of a computer system 3200. This system is exemplary only and one having skill in the art will recognize that variations and modifications are possible. The system 3200 can be used for the operations described above. For example, the computer systems shown in FIG. 32 may be used to implement any or all of the initialization (e.g., face annotation, skull fitting, constraint creation) and stabilization (e.g., skin energy or error determination, nose energy or error determination) techniques and routines described herein.

The system 3200 includes a processor 3210, a memory 3220, a storage device 3230, and an input/output interface 3240. Each of the components 3210, 3220, 3230, and 3240 are interconnected using a system bus 3250. The processor 3210 is capable of processing instructions for execution within the system 3200. In one implementation, the processor 3210 is a single-threaded processor. In another implementation, the processor 3210 is a multi-threaded processor. The processor 3210 is capable of processing instructions stored in the memory 3220 or on the storage device 3230 to provide graphical information via input/output interface 3240 for display on a user interface of one or more input/output device 3260.

The memory 3220 stores information within the system 3200 and may be associated with various characteristics and implementations. For example, the memory 3220 may include various types of computer-readable medium such as volatile memory, a non-volatile memory and other types of memory technology, individually or in combination.

The storage device 3230 is capable of providing mass storage for the system 3200. In one implementation, the storage device 3230 is a computer-readable medium. In various different implementations, the storage device 3230 may be a floppy disk device, a hard disk device, an optical disk device, or a tape device.

The input/output device 3260 provides input/output operations for the system 3200. In one implementation, the input/output device 3260 includes a keyboard and/or pointing device. In another implementation, the input/output device 3260 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube), LCD (liquid crystal display), LED (light emitting diode) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other. Although a few implementations have been described in detail above, other modifications are possible.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

Where components are described as being configured to perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

A number of embodiments of the invention have been described. Nevertheless, it will be understood that various modification may be made without departing from the scope of the invention.

What is claimed is:

1. A computer-implemented method of generating an animation model of an object, comprising:
   obtaining one or more images of the object, the object including an opaque surface located behind a refractive surface;
   determining one or more reflection constraints, one or more refraction constraints, and one or more position constraints for constraining generation of a refractive surface representation;
   generating the refractive surface representation by optimizing a position of the refractive surface using the one or more position constraints and by optimizing one or more surface normals of the refractive surface using the one or more reflection constraints and the one or more refraction constraints; and
   generating the animation model of the object, the animation model including the reconstructed refractive surface representation, wherein the refractive surface representation represents the refractive surface in the animation model of the object.

2. The method of claim 1, further comprising reconstructing an opaque surface representation by undoing distortion introduced by the refractive surface, the opaque surface representation representing the opaque surface of the object.

3. The method of claim 1, wherein generating the refractive surface representation includes employing an optimization method using the one or more reflection constraints, the one or more refraction constraints, and the one or more position constraints.

4. The method of claim 1, wherein the one or more reflection constraints are determined by extracting, from the one or more images, light reflected from the refractive surface, wherein the one or more refraction constraints are determined by extracting, from the one or more images, one or more points on the opaque surface, and wherein the one or more position constraints include a point within a transition region between the refractive surface and an additional surface of the object.

5. The method of claim 1, wherein the one or more reflection constraints are obtained by shining one or more lights onto the refractive surface.

6. The method of claim 1, wherein the object includes an eye, the refractive surface includes a cornea part of the eye, and the opaque surface includes an iris part of the eye.

7. The method of claim 6, further comprising reconstructing a sclera representation using the one or more images, the sclera representation representing a sclera part of the eye.

8. The method of claim 1, wherein the object is submerged under water and the refractive surface includes a surface of the water.

9. The method of claim 1, wherein the object is cast under a layer of material and the refractive surface includes a surface of the material.

10. A system for generating an animation model of an object, comprising:
    a memory storing a plurality of instructions; and
    one or more processors configurable to:
        obtain one or more images of the object, the object including an opaque surface located behind a refractive surface;
        determine one or more reflection constraints, one or more refraction constraints, and one or more position constraints for constraining generation of a refractive surface representation;
        generate the refractive surface representation by optimizing a position of the refractive surface using the one or more position constraints and by optimizing one or more surface normals of the refractive surface using the one or more reflection constraints and the one or more refraction constraints; and
        generate the animation model of the object, the animation model including the reconstructed refractive surface representation, wherein the refractive surface representation represents the refractive surface in the animation model of the object.

11. The system of claim 10, further comprising reconstructing an opaque surface representation by undoing distortion introduced by the refractive surface, the opaque surface representation representing the opaque surface of the object.

12. The system of claim 10, wherein generating the refractive surface representation includes employing an optimization method using the one or more reflection constraints, the one or more refraction constraints, and the one or more position constraints.

13. The system of claim 10, wherein the one or more reflection constraints are determined by extracting, from the one or more images, light reflected from the refractive surface, wherein the one or more refraction constraints are determined by extracting, from the one or more images, one or more points on the opaque surface, and wherein the one or more position constraints include a point within a transition region between the refractive surface and an additional surface of the object.

14. The system of claim 10, wherein the object includes an eye, the refractive surface includes a cornea part of the eye, and the opaque surface includes an iris part of the eye.

15. A non-transitory computer-readable memory storing a plurality of instructions executable by one or more processors, the plurality of instructions comprising:
    instructions that cause the one or more processors to obtain one or more images of the object, the object including an opaque surface located behind a refractive surface;
    instructions that cause the one or more processors to determine one or more reflection constraints, one or more refraction constraints, and one or more position constraints for constraining generation of a refractive surface representation;
    instructions that cause the one or more processors to generating the refractive surface representation by optimizing a position of the refractive surface using the one or more position constraints and by optimizing one or more surface normals of the refractive surface using the one or more reflection constraints and the one or more refraction constraints; and
    instructions that cause the one or more processors to generate the animation model of the object, the animation model including the reconstructed refractive surface representation, wherein the refractive surface representation represents the refractive surface in the animation model of the object.

16. The non-transitory computer-readable memory of claim 15, further comprising reconstructing an opaque surface representation by undoing distortion introduced by the refractive surface, the opaque surface representation representing the opaque surface of the object.

17. The non-transitory computer-readable memory of claim 15, wherein generating the refractive surface representation includes employing an optimization method using the one or more reflection constraints, the one or more refraction constraints, and the one or more position constraints.

18. The non-transitory computer-readable memory of claim 15, wherein the one or more reflection constraints are determined by extracting, from the one or more images, light reflected from the refractive surface, wherein the one or more refraction constraints are determined by extracting, from the one or more images, one or more points on the opaque surface, and wherein the one or more position constraints include a point within a transition region between the refractive surface and an additional surface of the object.

19. The non-transitory computer-readable memory of claim 15, wherein the object includes an eye, the refractive surface includes a cornea part of the eye, and the opaque surface includes an iris part of the eye.

20. The non-transitory computer-readable memory of claim 19, further comprising instructions that cause the one or more processors to reconstruct a sclera representation using the one or more images, the sclera representation representing a sclera part of the eye.

* * * * *

UNITED STATES PATENT AND TRADEMARK OFFICE
CERTIFICATE OF CORRECTION

PATENT NO. : 9,649,026 B2
APPLICATION NO. : 14/550751
DATED : May 16, 2017
INVENTOR(S) : Pascal Bérard, Thabo Beeler and Derek Bradley It is certified that error appears in the above-identified patent and that said Letters Patent is hereby corrected as shown below:

On the Title Page

Item (71), subsection Applicant:
Replace "LUCASFILM ENTERTAINMENT COMPANY, LTD., San Francisco, CA (US)" with
--DISNEY ENTERPRISES, INC., Burbank, CA (US)--

Signed and Sealed this
Sixth Day of February, 2018

Joseph Matal
*Performing the Functions and Duties of the*
*Under Secretary of Commerce for Intellectual Property and*
*Director of the United States Patent and Trademark Office*